US012611131B2

(12) United States Patent
McClung et al.

(10) Patent No.: US 12,611,131 B2
(45) Date of Patent: Apr. 28, 2026

(54) ELECTROCARDIOGRAM APPARATUS

(71) Applicant: CB Innovations, LLC, Carlsbad, CA (US)

(72) Inventors: Christian McClung, Rancho Santa Fe, CA (US); Stephen Dunphy, Carlsbad, CA (US)

(73) Assignee: CB Innovations, LLC, Carlsbad, CA (US)

( * ) Notice: Subject to any disclaimer, the term of this patent is extended or adjusted under 35 U.S.C. 154(b) by 205 days.

(21) Appl. No.: 18/384,872

(22) Filed: Oct. 29, 2023

(65) Prior Publication Data
US 2024/0057918 A1      Feb. 22, 2024

Related U.S. Application Data

(60) Continuation-in-part of application No. 17/665,003, filed on Feb. 4, 2022, which is a continuation-in-part
(Continued)

(51) Int. Cl.
*A61B 5/282*          (2021.01)
*A61B 5/00*           (2006.01)
(Continued)

(52) U.S. Cl.
CPC .............. *A61B 5/282* (2021.01); *A61B 5/259* (2021.01); *A61B 5/303* (2021.01); *A61B 5/6841* (2013.01); *A61B 5/02* (2013.01); *A61B 5/0205* (2013.01); *A61B 5/021* (2013.01); *A61B 5/024* (2013.01); *A61B 5/08* (2013.01); *A61B 5/0803* (2013.01);
(Continued)

(58) Field of Classification Search
CPC ......... A61B 5/282; A61B 5/259; A61B 5/303; A61B 5/6841; A61B 5/338; A61B 5/271; A61B 5/318; A61B 5/308; A61B 5/333; A61B 5/256; A61B 5/28; A61B 5/257;
(Continued)

(56) References Cited

U.S. PATENT DOCUMENTS 4,353,372 A * 10/1982 Ayer .................. H01R 12/7076
174/268
5,161,539 A * 11/1992 Evans ...................... A61B 5/35
600/513
(Continued)

FOREIGN PATENT DOCUMENTS

WO      WO-2005041768 A1 *  5/2005   ............. A61B 5/282

OTHER PUBLICATIONS

Translation of WO 2005041768, May 12, 2005 (Year: 2005).*
International Search Report and Written Opinion for PCT Application PCT/US23/36220, mailed Apr. 15, 2024.

*Primary Examiner* — Adam Z Minchella
(74) *Attorney, Agent, or Firm* — Clause Eight; Michael Catania

(57) ABSTRACT

A diagnostic electrocardiogram (ECG) apparatus (20) is disclosed herein. The apparatus comprises a body and printed electrodes. The body (110) includes extension members (61-66), with each having an expansion section (61a) and at least one electrode section (61b). Each expansion section (61a) has at least one concertina member (75) and at least one connector member (76). The diagnostic ECG apparatus (20) conforms to American Heart Association guidelines on diagnostic resting ECGs.

5 Claims, 32 Drawing Sheets

Related U.S. Application Data of application No. 17/106,125, filed on Nov. 29, 2020, now Pat. No. 12,446,817, and a continuation-in-part of application No. 16/812,330, filed on Mar. 8, 2020, now Pat. No. 11,896,393, which is a continuation-in-part of application No. 15/990,651, filed on May 27, 2018, now Pat. No. 10,881,313, said application No. 17/106,125 is a division of application No. 15/904,411, filed on Feb. 25, 2018, now Pat. No. 10,893,818, which is a continuation-in-part of application No. 15/853,578, filed on Dec. 22, 2017, now Pat. No. 9,986,929, said application No. 15/990,651 is a continuation of application No. 15/853,578, filed on Dec. 22, 2017, now Pat. No. 9,986,929.

(60) Provisional application No. 63/421,569, filed on Nov. 2, 2022, provisional application No. 63/147,191, filed on Feb. 8, 2021, provisional application No. 62/825,018, filed on Mar. 27, 2019, provisional application No. 62/819,025, filed on Mar. 15, 2019, provisional application No. 62/530,144, filed on Jul. 8, 2017, provisional application No. 62/465,752, filed on Mar. 1, 2017.

(51) Int. Cl.

| | |
|---|---|
| *A61B 5/259* | (2021.01) |
| *A61B 5/28* | (2021.01) |
| *A61B 5/30* | (2021.01) |
| *A61B 5/02* | (2006.01) |
| *A61B 5/0205* | (2006.01) |
| *A61B 5/021* | (2006.01) |
| *A61B 5/024* | (2006.01) |
| *A61B 5/08* | (2006.01) |
| *A61B 5/256* | (2021.01) |
| *A61B 5/257* | (2021.01) |
| *A61B 5/271* | (2021.01) |
| *A61B 5/308* | (2021.01) |
| *A61B 5/316* | (2021.01) |
| *A61B 5/318* | (2021.01) |
| *A61B 5/333* | (2021.01) |
| *A61B 5/338* | (2021.01) |

(52) U.S. Cl.
CPC .............. *A61B 5/256* (2021.01); *A61B 5/257* (2021.01); *A61B 5/271* (2021.01); *A61B 5/28* (2021.01); *A61B 5/308* (2021.01); *A61B 5/316* (2021.01); *A61B 5/318* (2021.01); *A61B 5/333* (2021.01); *A61B 5/338* (2021.01); *A61B 2505/01* (2013.01); *A61B 2562/02* (2013.01); *A61B 2562/0209* (2013.01); *A61B 2562/04* (2013.01); *A61B 2562/046* (2013.01); *A61B 2562/222* (2013.01); *A61B 2562/227* (2013.01)

(58) Field of Classification Search
CPC ......... A61B 5/316; A61B 5/02; A61B 5/0205; A61B 5/021; A61B 5/024; A61B 5/08
See application file for complete search history.

(56) References Cited

U.S. PATENT DOCUMENTS

| | | | | |
|---|---|---|---|---|
| 6,453,186 | B1 * | 9/2002 | Lovejoy ................. | A61B 5/282 |
| | | | | 600/386 |
| 6,847,836 | B1 * | 1/2005 | Sujdak ................... | A61B 5/282 |
| | | | | 600/382 |
| 9,893,438 | B1 | 2/2018 | Oster et al. | |
| 2008/0009754 | A1 * | 1/2008 | Chang ................... | A61B 5/742 |
| | | | | 600/483 |
| 2008/0177168 | A1 * | 7/2008 | Callahan ............. | A61B 5/6841 |
| | | | | 600/382 |
| 2010/0160762 | A1 * | 6/2010 | McLaughlin .......... | A61B 5/273 |
| | | | | 600/372 |
| 2011/0048772 | A1 | 3/2011 | Han | |
| 2011/0077497 | A1 * | 3/2011 | Oster .................... | A61B 5/259 |
| | | | | 600/300 |
| 2017/0281925 | A1 * | 10/2017 | Silver ................. | A61B 5/6843 |
| 2018/0213859 | A1 * | 8/2018 | LaPlante ........... | A41D 13/1236 |
| 2019/0298987 | A1 * | 10/2019 | Freeman ............. | A61N 1/0484 |
| 2021/0113133 | A1 | 4/2021 | Dunphy et al. | |
| 2022/0022796 | A1 * | 1/2022 | Cho ..................... | A61B 5/002 |
| 2022/0175292 | A1 | 6/2022 | McClung et al. | |

* cited by examiner

ELECTROCARDIOGRAM APPARATUS

CROSS REFERENCES TO RELATED APPLICATIONS

The Present Application claims priority to U.S. Provisional Patent Application No. 63/421,569, filed on Nov. 2, 2022, and is a continuation-in-part application of U.S. patent application Ser. No. 17/665,003, filed on Feb. 4, 2022, which claims priority to U.S. Provisional Patent Application No. 63/147,191, filed on Feb. 8, 2021, which is a continuation-in-part application of U.S. patent application Ser. No. 16/812,330, filed on Mar. 8, 2020, which claims priority to U.S. Provisional Patent Application No. 62/819,025 filed on Mar. 15, 2019, and U.S. Provisional Patent Application No. 62/825,018 filed on Mar. 27, 2019, and U.S. patent application Ser. No. 16/812,330 is a continuation-in-part application of U.S. patent application Ser. No. 15/990,651, filed on May 27, 2018, now U.S. patent Ser. No. 10/881,313, which is a continuation application of U.S. patent application Ser. No. 15/853,578, filed on Dec. 22, 2017, now U.S. Pat. No. 9,986,929, issued on Jun. 5, 2018, which claims priority to U.S. Provisional Patent Application No. 62/465,752, filed on Mar. 1, 2017, and also claims priority to 62/530,144, filed on Jul. 8, 2017, each of which is hereby incorporated by reference in its entirety, and U.S. patent application Ser. No. 17/665,003 is a continuation-in-part application of U.S. patent application Ser. No. 17/106,125, filed on Nov. 29, 2020, which is a divisional of U.S. patent application Ser. No. 15/904,411, filed on Feb. 25, 2018, now U.S. patent Ser. No. 10/893,818, issued on Jan. 19, 2021, which is a continuation-in-part application of U.S. patent application Ser. No. 15/853,578, filed on Dec. 22, 2017, now U.S. Pat. No. 9,986,929, issued on Jun. 5, 2018, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to ECG devices.

Description of the Related Art

The electrocardiogram (ECG) is an essential test that provides medical professionals with essential information in the management of patients with a variety of conditions. It is not only of significant importance in the evaluation and management of patients with chest pain, but also in patients with shortness of breath, syncope, dizziness, seizures, altered mental status, stroke, psychiatric conditions, overdose, palpitations and many other conditions. It is a bulky system with a multitude of wires and connections.

The ECG provides critical data to the health care provider in managing patients with multiple medical issues. The time to obtain this data is critical and often delayed by the current technology. Minutes can become critical in the patient with an acute myocardial infarction (heart attack).

Historically, there is training in the interpretation of ECG data, as well as placement of electrodes on the chest of each patient in anatomically specific positions.

Current ECG placement is done by technicians and providers of varying medical background, including paramedics, health care technicians, nursing assistants, nurses, and doctors. The current technology is bulky, with many wires and cables. The placement of the electrodes in the acquisition of an ECG is specific and requires special training. ECG acquisition is often limited and/or delayed by multiple factors such as body sweat, ability to transport the ECG device into confined areas, performance of concomitant medical procedures such as cardiopulmonary resuscitation (CPR). Because of many limitations, medical providers must make rapid decisions and potentially delay medical care while ECG testing is done. As emergency medicine providers, the inventors have identified a need for more rapid placement of the ECG electrodes, a more portable and manageable system that will not compromise medical care, and the need to eliminate electrode placement errors.

Sujdak, U.S. Pat. No. 6,847,836 for an Emergency ECG Electrode Chest Pad discloses a chest pad adapted for use in an emergency room.

Dominguez, U.S. Pat. No. 6,560,473 for a Disposable ECG Chest Electrode Template With Built-In Defibrillation Electrodes discloses a template that carries ten electrodes.

The acquisition of a 12-lead ECG requires accurate placement of electrodes and avoidance of lead transposition. This has been a challenge for many healthcare workers and staff that place ECG electrodes. For lay persons outside of the healthcare setting this requires expertise not typically expected of the general population. Heart disease is still the number one cause of death in the United States. With an ever-increasing aged population, the timely diagnosis of heart disease and risk stratification is key to improved morbidity and mortality. The 12-lead ECG is central to this diagnosis and management. Technology is enabling extension of the health care continuum to expand into the home and away from a hospital or clinical setting. With a population of educated patients that value time and utility of their health care data, the ability to transmit and interpret reliable ECG data outside of the standard health care setting allows patients to take even more ownership of their health.

BRIEF SUMMARY OF THE INVENTION

The motivation for the present invention is to a device capable of making diagnostic electrocardiogram access to a population both within and outside traditional health care settings, thus enabling a diagnostic quality ECG to be obtained that conforms to American Heart Association guidelines on diagnostic resting ECGs and also capable of obtaining continuous diagnostic ECG monitoring and acquisition during times of exercise and exertion. The device allows for electrode placement in key positions that conform to proximal limb positions and precordial chest positions that allow for a diagnostic-quality ECG to be obtained. Further, the device allows for this to be applied by both lay persons and medically trained staff.

The present invention incorporates screen-printed ECG electrodes and conducting circuits into a stretchable, and elastic device with integrated electrical conducting materials that transfer physiologic electrical signals to a central processing unit for ECG acquisition and interpretation. The device is available in multiple sizes to accommodate different body types.

One aspect of the present invention is a diagnostic electrocardiogram (ECG) apparatus. The apparatus comprises a body and printed electrodes. The body comprises a plurality of extension members. Each of the plurality of extension members comprises an expansion section and at least one electrode section. The printed electrodes are positioned on the body. Each of the at least one electrode sections of the extension members has a screen printed electrode of the printed electrodes.

Another aspect of the present invention is an emergency cardiac and electrocardiogram (ECG) electrode placement device. The device comprises a body and printed electrodes. The body comprises extension members. The body comprises a base layer composed of an unwoven fabric material, an adhesive layer composed of a flexible material, and a backing layer attached to an adhesive surface of the adhesive layer. Each of the extension members comprises an expansion section and at least one electrode section. Each of the extension members extend outward from a center of the body for proper placement of the electrodes on a patient.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

Figure 5:
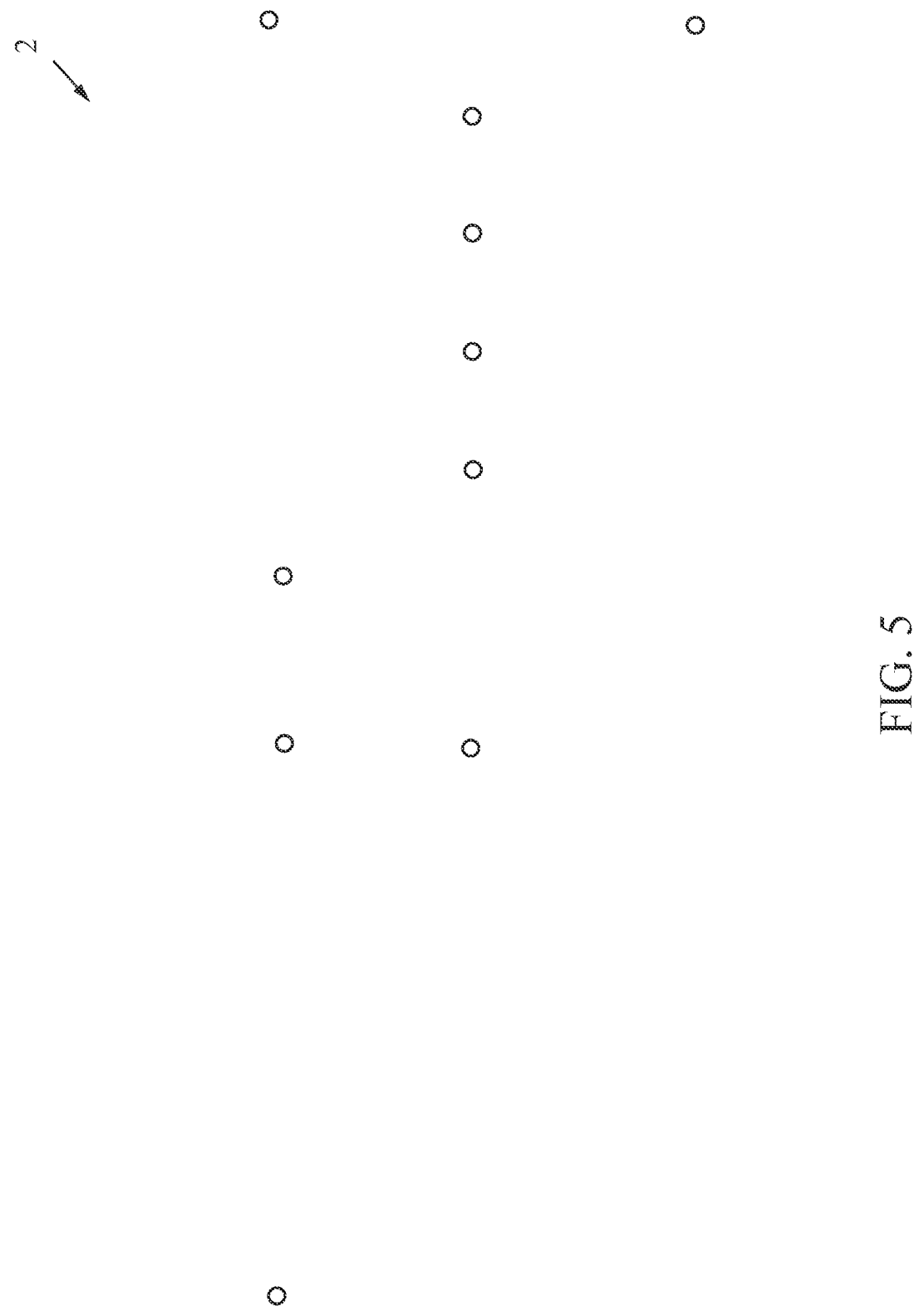

FIG. 5 is an isolated view of AgCl placement for an emergency cardiac and ECG electrode device.

Figure 10:
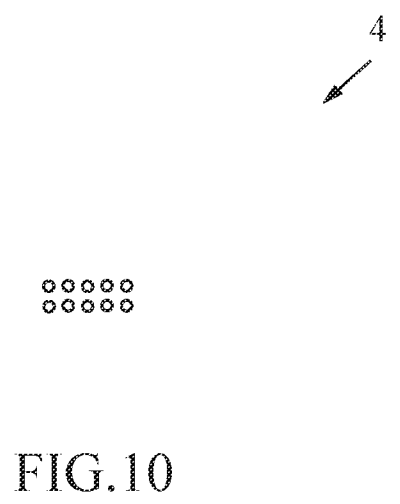

FIG. 10 is an isolated view of the carbon contacts for an emergency cardiac and ECG electrode device.

DETAILED DESCRIPTION OF THE INVENTION

Figure 1:
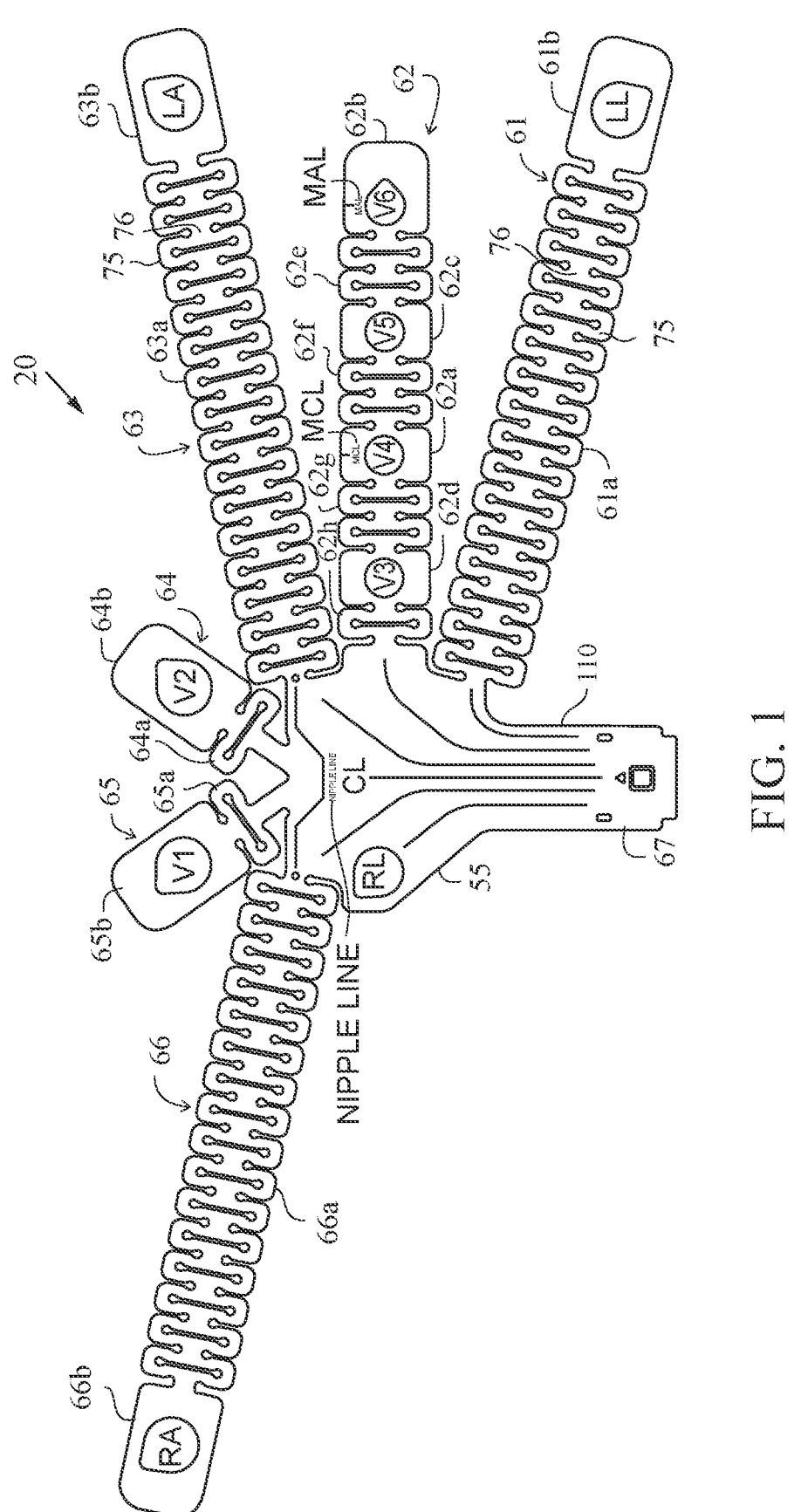
FIG. 1 illustrates a top plan view of an emergency cardiac and ECG electrode device with placement markers.

As shown in FIGS. 1-11 and FIG. 24, an emergency cardiac and ECG electrode device 20 worn by a user comprises a central body 110, a first extension 61, a second extension 62, a third extension 63, a fourth extension 64, a fifth extension 65 and a sixth extension 66. The ECG electrode device 20 also comprises screen-printed electrodes 115 (designated in FIG. 1 as LL, V3, V4, V5, V6, LA, V2, V1, RA and RL) with corresponding screen-printed wires 105. The screen-printed electrodes 115 (V1-V6, LL, LA, RA, RL) are positioned on an internal surface of the ECG electrode device 20. An electrode connector 170 (shown in FIG. 28) preferably connects to the end of the lower extension 67 of the central body 110. The screen-printed wires 105 are positioned in the ECG electrode device 20, and each of the wires 105 is connected from a connection extension 67 to an electrode 115 V1-V6.

The body 110 of the device 20 has a thickness preferably ranging from 0.3 mm to 1.5 mm, more preferably 0.05 mm to 1.0 mm, and most preferably 0.84 mm.

Each of the plurality of extension members comprises an expansion section and at least one electrode section. The expansion section of each of the plurality of extension members comprises at least one concertina member integrated with at least one connector member. Each expansion section of the plurality of extension members comprises 1 to 20 concertina members. At least one extension member comprises a plurality of expansions sections and a plurality of electrode sections. The body has plurality of contacts positioned on an end portion of the center section of the body. Each of the plurality of contacts is preferably composed of an abrasive resistant ink. Each of the plurality of extension members is preferably configured for at least double length extension from an un-extended state, alternatively 50% extension from an un-extended state, and preferably at least a 25% extension from an un-extended state. The body preferably comprises a layer of an unwoven fabric. Each of the plurality of printed wires and each of the printed electrodes is preferably composed of a printable conductive silver.

Figure 2:
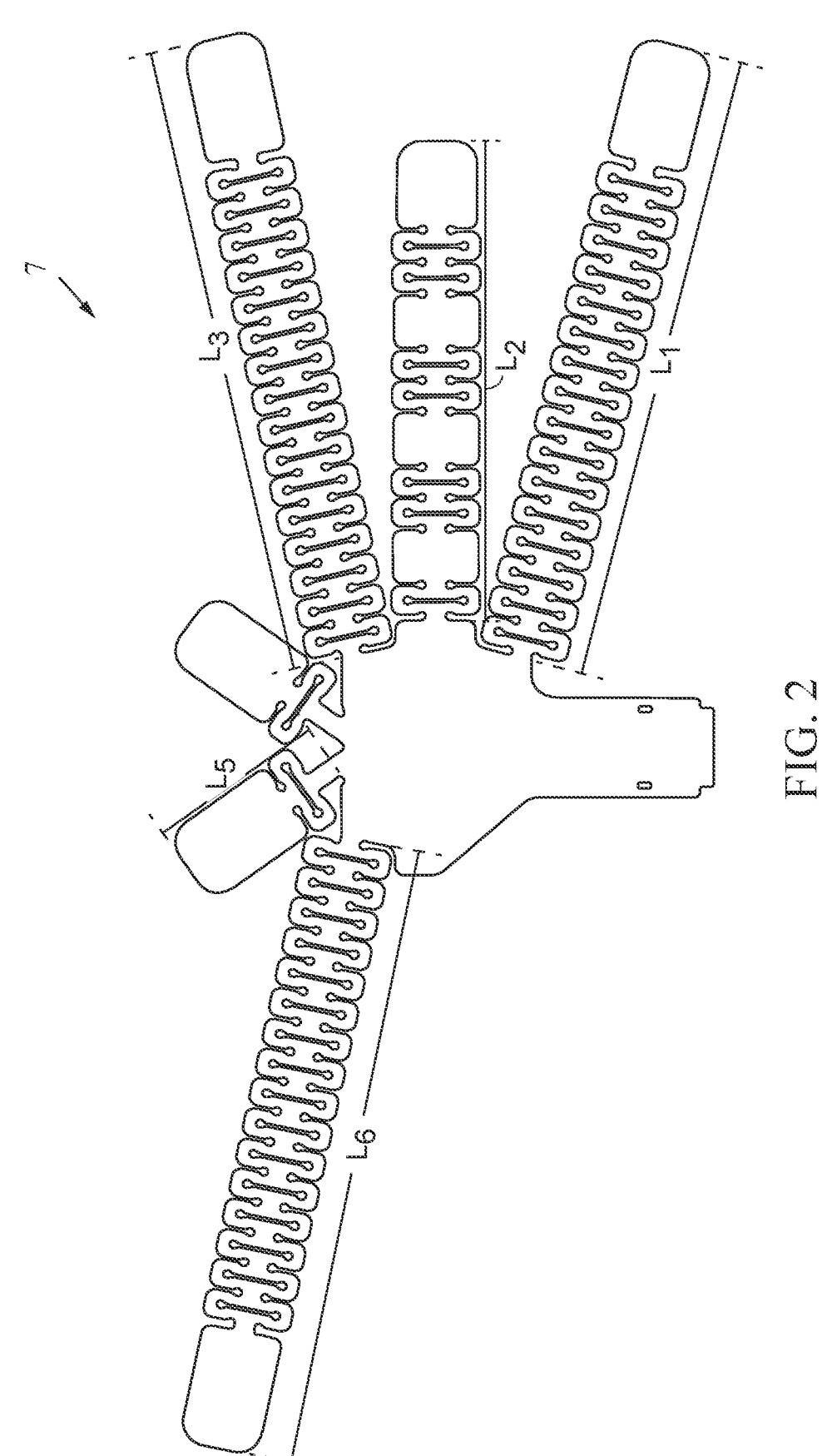
FIG. 2 illustrates a top plan view of a polyester layer of an emergency cardiac and ECG electrode device.

The first extension member 61 has an expansion section 61a and an electrode section 61b. The expansion section 61a preferably has sixteen concertina members 75 and seventeen connector members 76. One connector member 76 connects a concertina member 75 to the electrode section 61b. The first extension member 61 has a resting (un-extended from the end of the electrode section 61b to the connection to the central body 55 (L1 as shown in FIG. 2) length preferably ranging from 20 centimeters (cm) to 30 cm, more preferably ranging from 21 to 25 cm, and most preferably 23 cm. The width of the first extension member 61 is preferably 1 cm to 4 cm, more preferably 2 cm to 3.5 cm, and most preferably 3 cm.

The second extension member 62 has expansion sections 62e, 62f, 62g and 62h, and electrode sections 62a, 62b, 62c and 62d. The extension member 62 preferably has expansion sections between electrode sections. The second extension member 62 has a resting (un-extended from the end of the electrode section 62b to the connection to the central body 55 (L2 as shown in FIG. 2) length preferably ranging from 15 cm to 25 cm, more preferably ranging from 16 to 20 cm, and most preferably 18 cm. The width of the second extension member 62 is preferably 1 cm to 4 cm, more preferably 2 cm to 3.5 cm, and most preferably 3 cm.

The third extension member 63 preferably has an expansion section 63a and an electrode section 63b. The expansion section 63a preferably has sixteen concertina members 75 and seventeen connector members 76. The third extension member 63 has a resting (un-extended from the end of the electrode section 63b to the connection to the central body 55 (L3 as shown in FIG. 2) length preferably ranging from 20 cm to 30 cm, more preferably ranging from 21 to 25 cm, and most preferably 23 cm. The width of the third extension member 63 is preferably 1 cm to 4 cm, more preferably 2 cm to 3.5 cm, and most preferably 3 cm.

The fourth extension member 64 preferably has an expansion section 64a and an electrode section 64b. The expansion section 64a preferably has one concertina member 75 and one connector member. The fourth extension member 64 has a resting (un-extended from the end of the electrode section 64b to the connection to the central body 55 length preferably ranging from 3 cm to 10 cm, more preferably ranging from 4 cm to 8 cm, and most preferably 7 cm. The width of the third extension member 64 is preferably 1 cm to 4 cm, more preferably 2 cm to 3.5 cm, and most preferably 3 cm.

The fifth extension member 65 preferably has an expansion section 65a and an electrode section 65b. The expansion section 65a preferably has one concertina member 75 and one connector member. The fifth extension member 65 has a resting (un-extended from the end of the electrode section 65b to the connection to the central body 55 length (L5 in FIG. 2) preferably ranging from 3 cm to 10 cm, more preferably ranging from 4 cm to 8 cm, and most preferably 7 cm. The width of the third extension member 65 is preferably 1 cm to 4 cm, more preferably 2 cm to 3.5 cm, and most preferably 3 cm.

The sixth extension member 66 has an expansion section 66a and an electrode section 66b. The expansion section 66a preferably has sixteen concertina members 75 and seventeen connector members 76. The sixth extension member 66 has a resting (un-extended from the end of the electrode section 66b to the connection to the central body 55 (L6 as shown in FIG. 2) length preferably ranging from 20 cm to 30 cm, more preferably ranging from 21 to 25 cm, and most preferably 23 cm. The width of the sixth extension member 66 is preferably 1 cm to 4 cm, more preferably 2 cm to 3.5 cm, and most preferably 3 cm.

Each concertina member 75 is preferably rectangular in shape with and central aperture, allowing for extension of the extension member. Each concertina member 75 preferably has a first side panel, a second side panel parallel to the first side panel, a third side panel perpendicular and connecting to first ends of the first side panel and the second side panel, and a fourth side panel parallel to the third side panel and connecting to the second ends of the first side panel and the second side panel. The first side panel, the second side panel, the third side panel and the fourth side panel define the central aperture.

Those skilled in the pertinent are will recognize that the extension members may have alternative numbers of expansion sections and electrode sections, and alternative numbers of concertina members and connector members without departing from the scope and spirit of the present invention.

The ECG device 20 is preferably a 12 lead ECG. The screen-printed electrodes 115 are preferably comprised of ten electrodes indexed to meet American Heart Association (AHA) guidelines for diagnostic criteria 12-lead ECG and additional node positions for diagnostic studies for right sided interpretation and posterior interpretation lead positioning.

Figure 11:
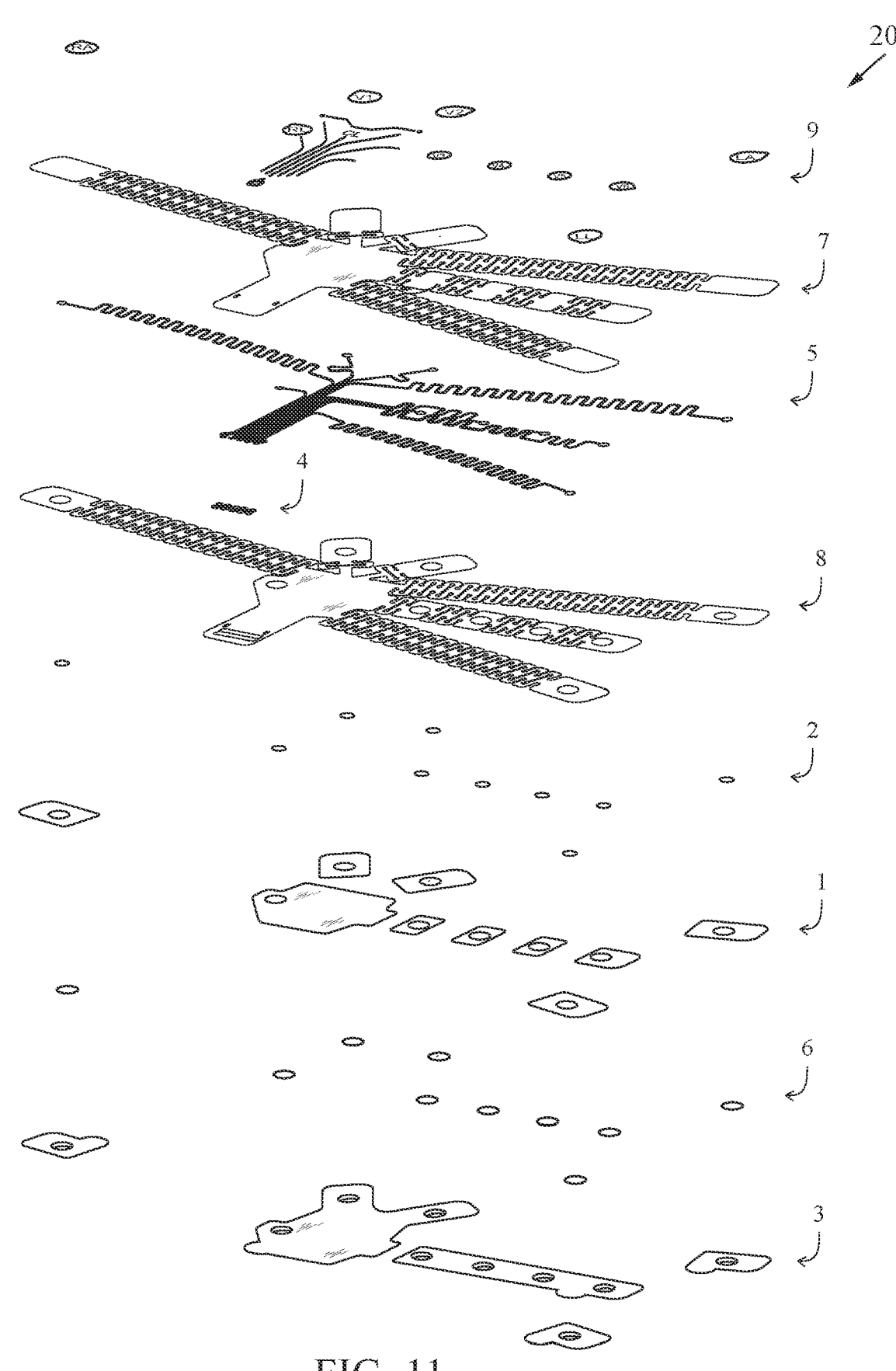
FIG. 11 is an exploded view of an emergency cardiac and ECG electrode device.

FIG. 11 is an exploded view of an emergency cardiac and ECG electrode device 20. The ECG device 20 comprises of placement markers 9, a polyester layer 7, wired circuits (printed silver tracing) 5, carbon contacts 4, an unwoven fabric layer 8, an AgCl components layer 2, an adhesive layer 1, a hydrogel components layer 6, and a backing liner layer 3. A dielectric layer is not shown.

Figure 12:
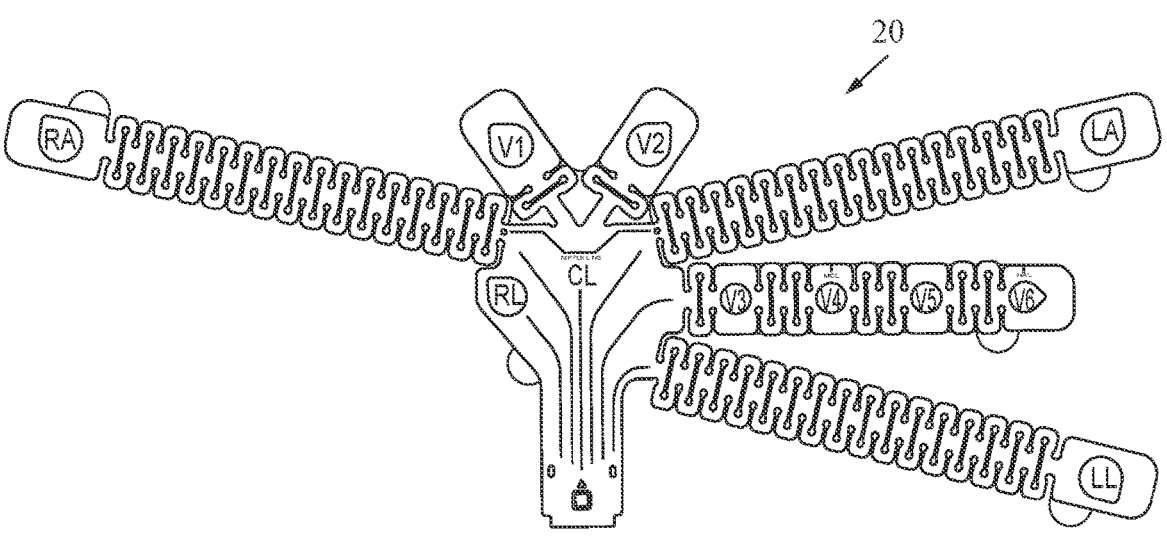
FIG. 12 is a top plan view of an emergency cardiac and ECG electrode device.
Figure 13:
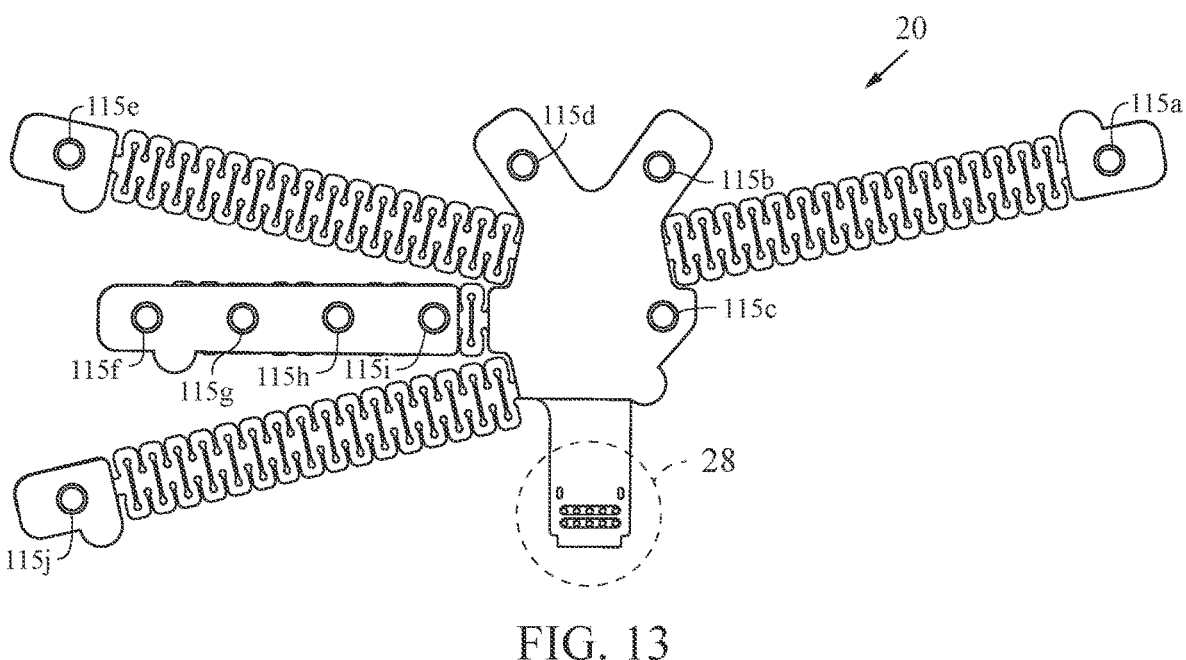
FIG. 13 is a bottom plan view of an emergency cardiac and ECG electrode device.

The assembled emergency cardiac and ECG electrode device 20 of FIG. 11 is shown in FIG. 12, top view, and in FIG. 13, bottom view showing electrodes 115a-115j.

Figure 25:
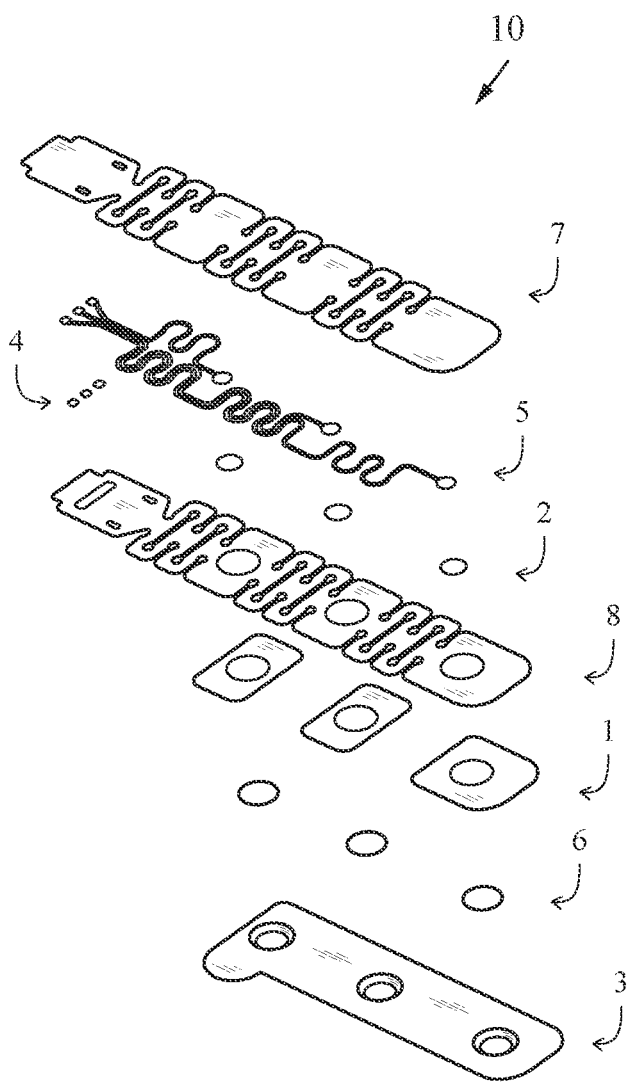
FIG. 25 is an exploded view of 3 lead component.

FIG. 25 illustrates a 3 lead component 10 that allows for the 12 Lead ECG device to expand to a 15 lead ECG device. The 3 lead component 10 comprises of a polyester layer 7, wired circuits (printed silver tracing) 5, carbon contacts 4, an AgCl components layer 2, an unwoven fabric layer 8, an adhesive layer 1, a hydrogel components layer 6, and a backing liner layer 3. A dielectric layer is not shown.

Figure 26:
FIG. 26 is a side view of the 3 lead component.
Figure 27:
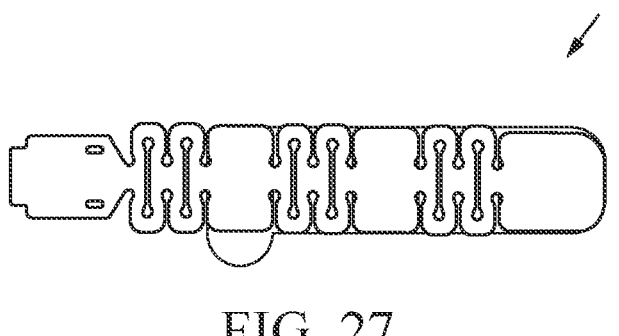
FIG. 27 is a top plan view of the 3 lead component.

The assembled 3 lead component 10 of FIG. 25 is shown in FIG. 27, top view, and in FIG. 26, side view. The 3 lead component 10 has a resting (un-extended from the end of the farthest electrode section to the connection to the central body) length preferably ranging from 15 cm to 25 cm, more preferably ranging from 16 to 20 cm, and most preferably 18 cm. The width of the 3 lead component 10 is preferably 1 cm to 4 cm, more preferably 2 cm to 3.5 cm, and most preferably 3 cm In one embodiment, the device 20, herein referenced also as EXGEES12L (EXG), is an intuitively designed EKG sticker. It uses only one connection point versus the 10 separate cables typical of an EKG. The electrodes are incorporated into the device that uses embedded circuitry to carry the signal to a common connection region. The device 20 is compliant with ANSI AAMI EC12 and EC53 guidelines, and designed to be a sticker with medical grade hypoallergenic adhesive that is applied to clean, intact skin. It is a single patient use device and can remain on the patient for up to 24 hours of continuous typical hospital stay use.

The expandable design is made to fit most adults from the 5th to 95th percentile body sizes. The electrodes are placed in the standard American Heart association approved locations (e.g., below the shoulders, below the hip and in the ascribed precordial regions.

Figure 3:
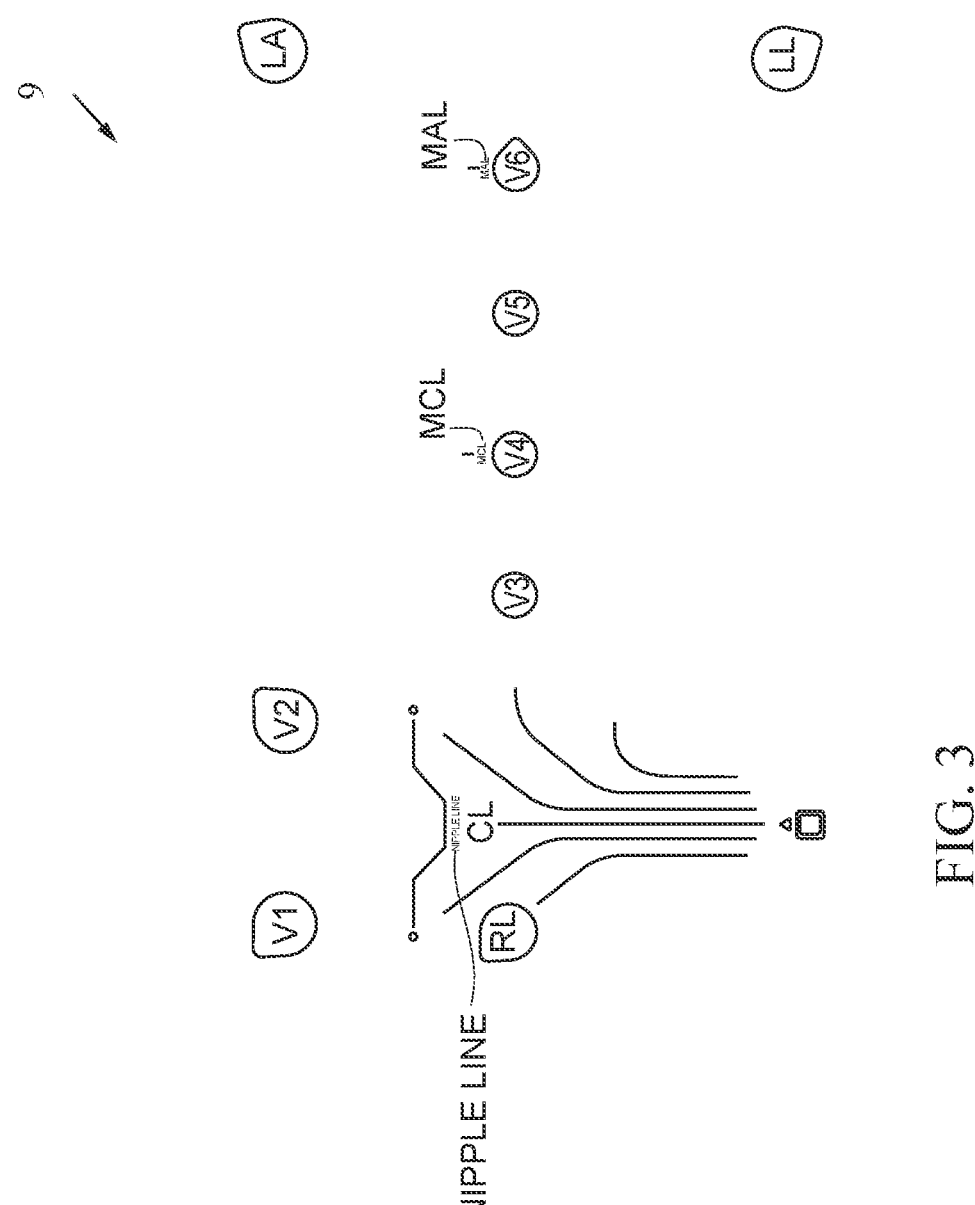
FIG. 3 is an illustration of placement stickers for an emergency cardiac and ECG electrode device.
Figure 4:
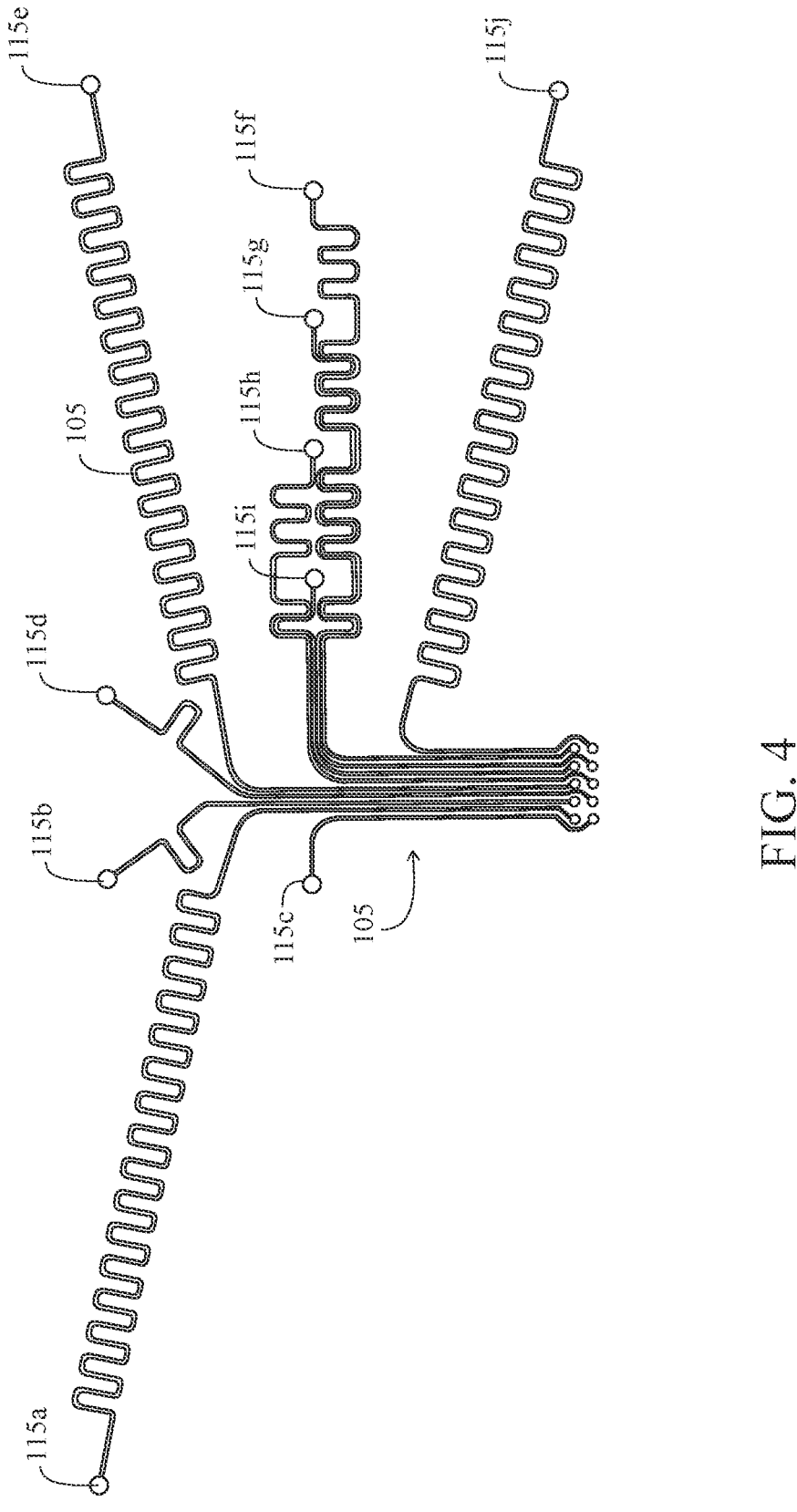
FIG. 4 is an isolated view of wiring for an emergency cardiac and ECG electrode device.
Figure 6:
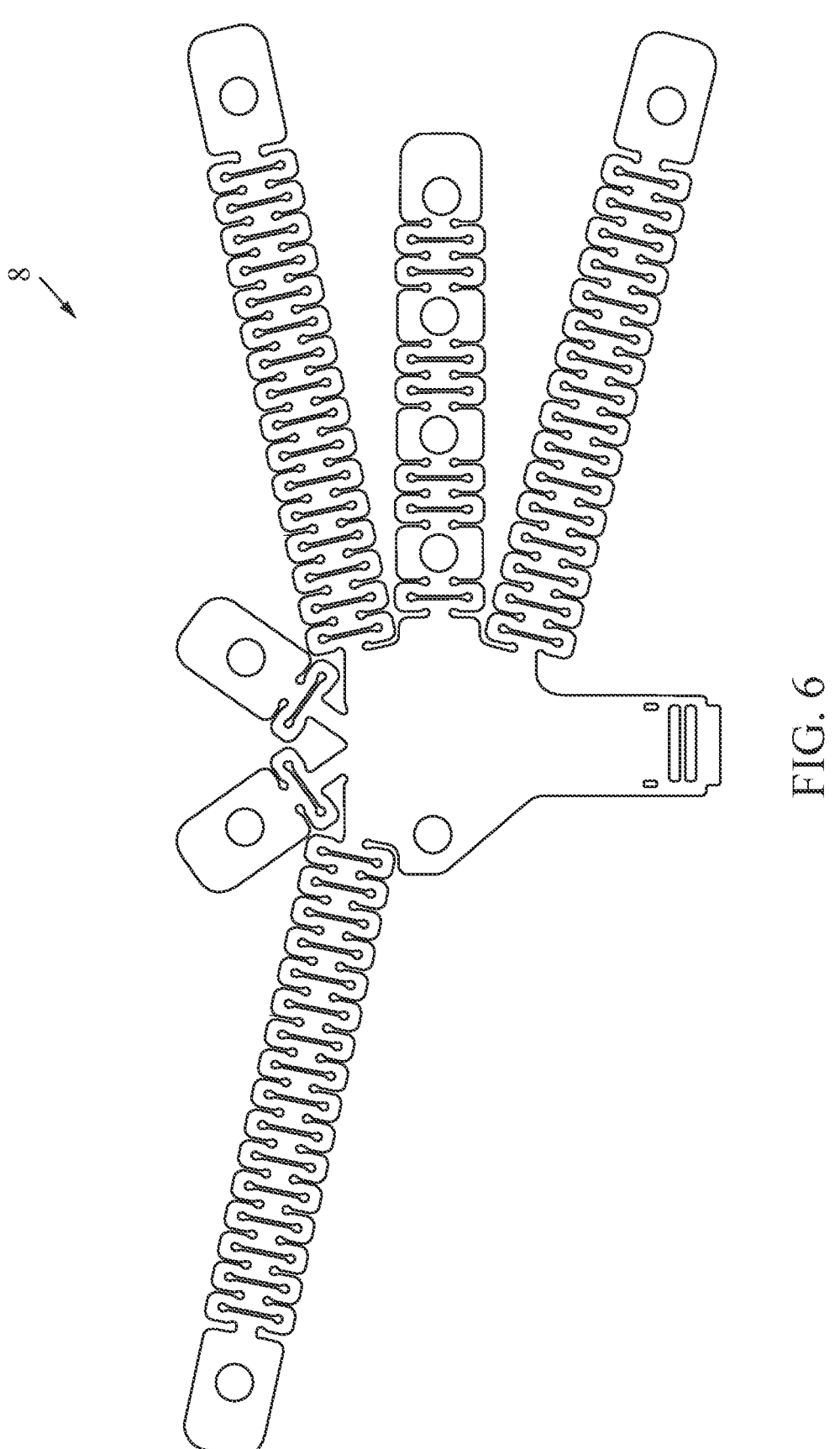
FIG. 6 illustrates a top plan view of an unwoven fabric layer of an emergency cardiac and ECG electrode device.
Figure 7:
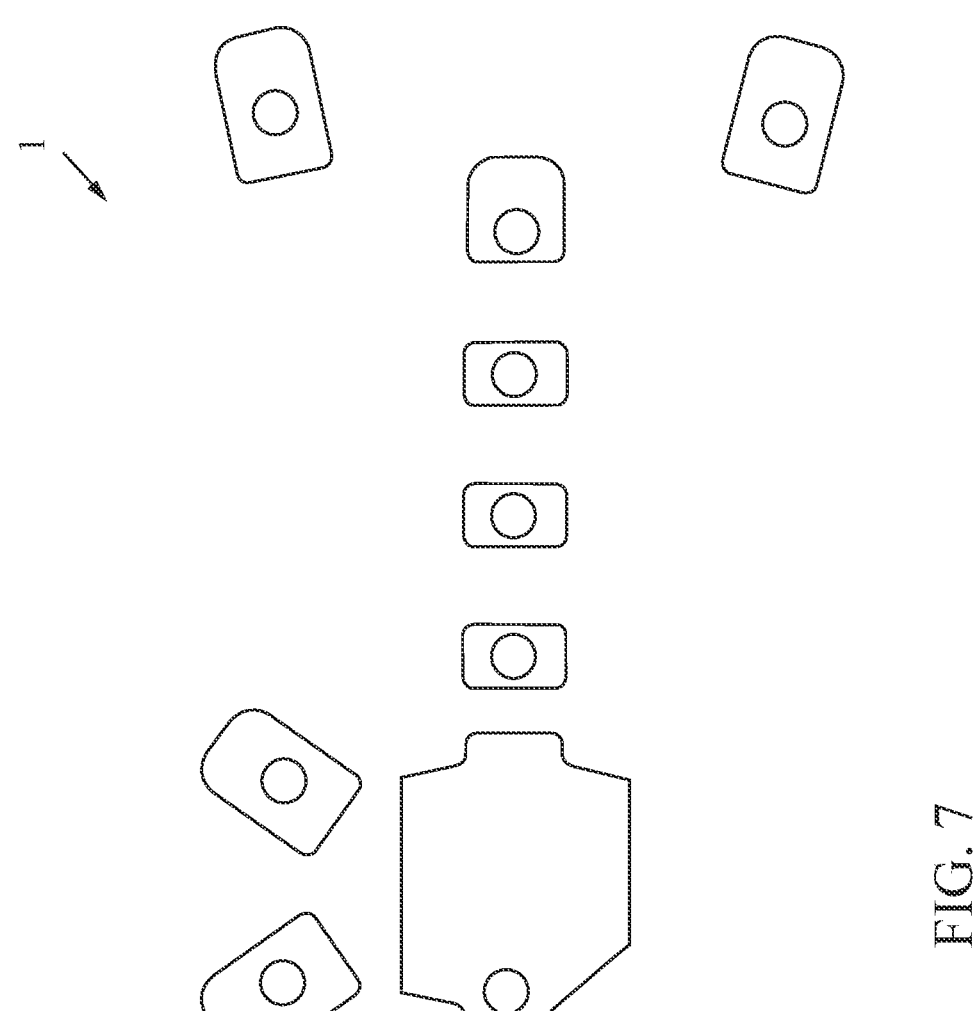
FIG. 7 is an isolated view of the adhesive layers for an emergency cardiac and ECG electrode device.
Figure 7:
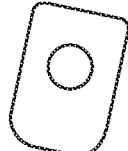
Figure 8:
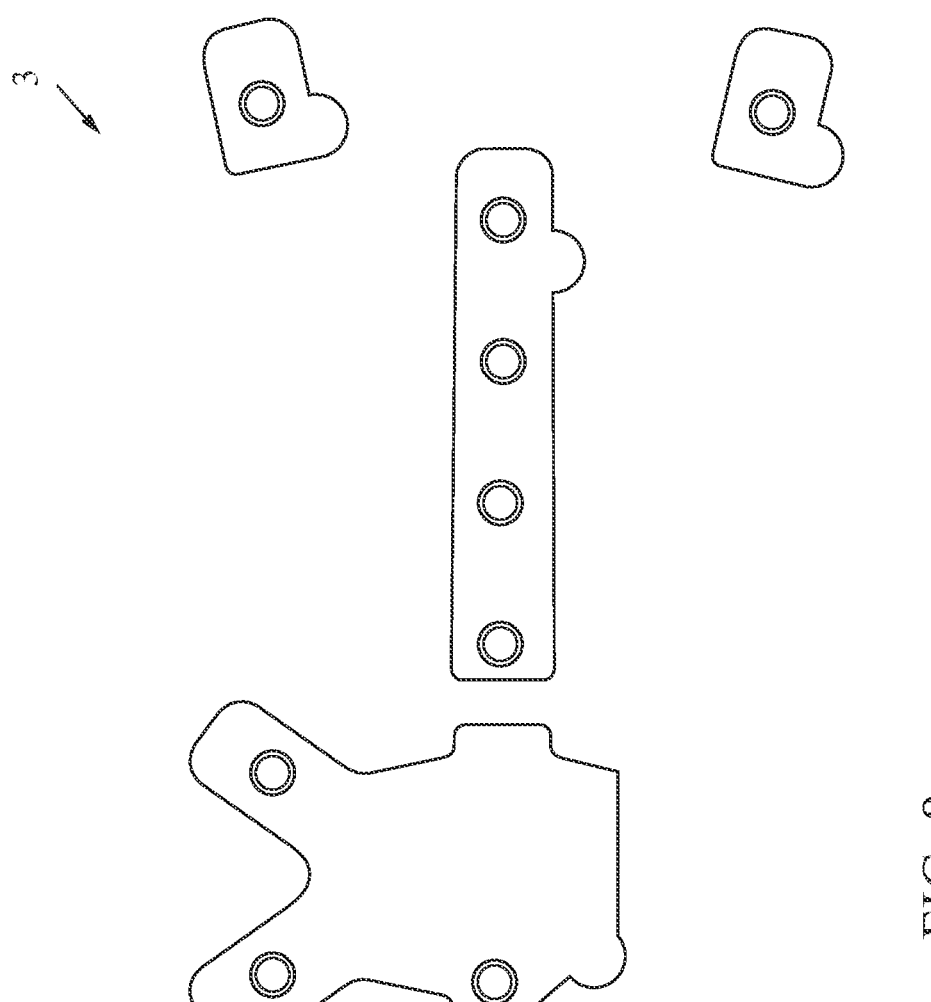
FIG. 8 is an isolated view of the backing layers for an emergency cardiac and ECG electrode device.
Figure 8:
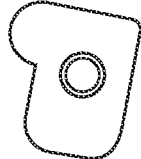
Figure 9:
FIG. 9 is an isolated view of the hydrogel placement for an emergency cardiac and ECG electrode device.

The device is well labeled with placement markers 9, shown in FIG. 1 and FIG. 3, in accordance with AHA guidelines. Additionally, there are markers for the nipple line, a V4 marker for the mid clavicular line (MCL), and a V6 marker with mid axillary line (MAL), as shown in FIGS. 1 and 3. The center sticker is indexed to align with the ideal nipple line. The device is easily applied by medically trained staff as well as lay persons. The device is intuitively designed and goes on quickly and is comfortable. The embedded electrode and integrated cable design allows connection to existing 12 lead, 6 lead, 5 lead and 3 lead systems with the appropriate adapter. The EXG 20 will connect via a single point to an adapter for integration into existing cardiac monitors and devices. The electrodes will be AgCL and measure 8-10 mm in diameter. The electrodes will be covered with a hydrogel type material 13-15 mm in diameter.

The EXG 20 will adhere to the chest wall and ascribed electrode locations. The EXG 20 will remain on the patient and tolerate motion such as seen in running and walking and other physiologic changes such as perspiration, diaphoresis. The EXG 20 electrode circuitry will be printed with conductive flexible inks that are 1-2 mm thickness. The EXG electrode connection point will be resistant to scuff, scratch and inadvertent abrasion preventing transmission. The EXG 20 connection terminus will be intuitively loaded into the appropriate universal adapter.

The EXG 20 will be hermetically packaged and labeled in accordance with above guidelines. The EXG 20 will have a shelf life of preferably more than 24 months in packaging and more than 29 days out of packaging if unused, with backing intact.

The EXG 20 backing will prevent inadvertent desiccation of the adhesive and hydrogel. The backing will be intuitive with pull tabs for ergonomic use. The pull tabs will be located at the limb electrodes, the base of the central area, and at V6.

Figure 16:
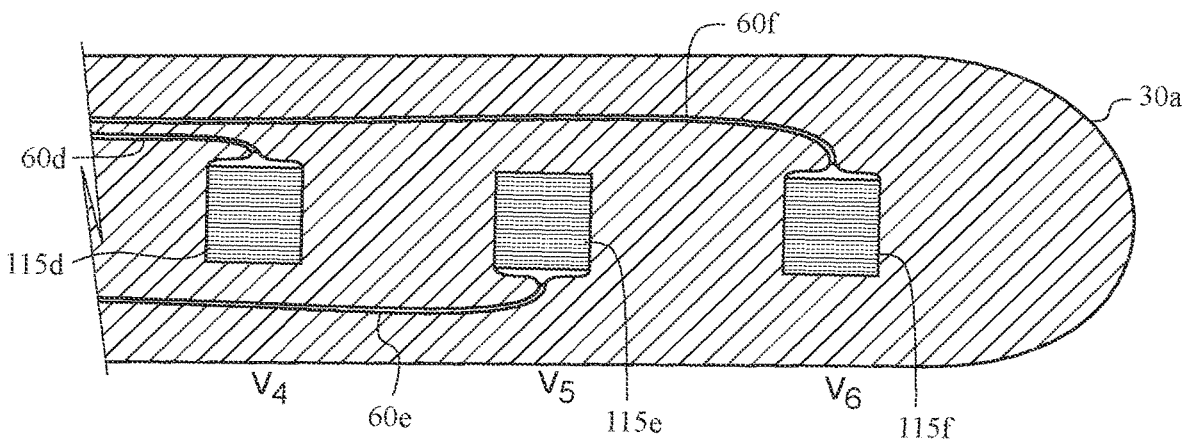
FIG. 16 is an isolated top plan view of a top surface of an extension of an emergency cardiac and ECG electrode placement device.
Figure 17:
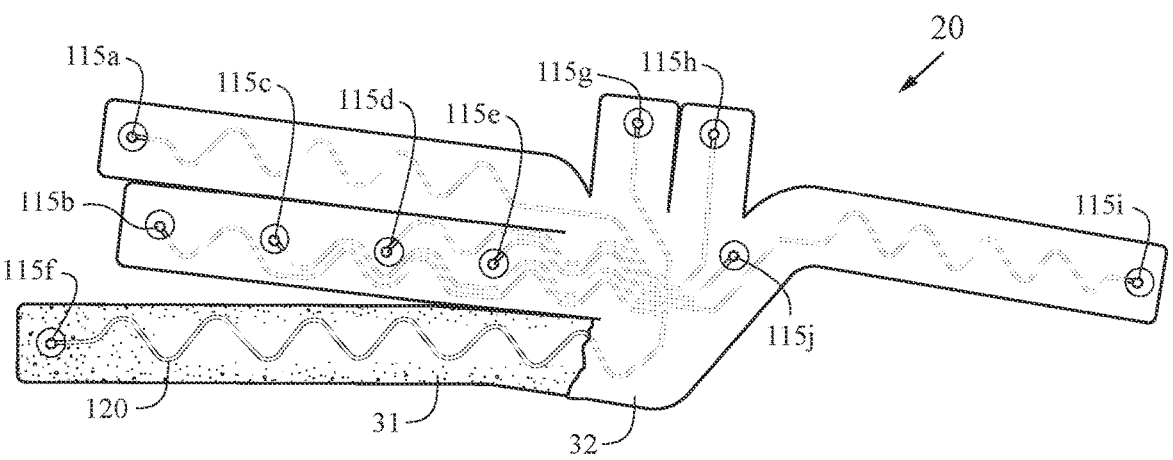
FIG. 17 is a bottom plan view of a multi-electrode screen-printed design.
Figure 18:
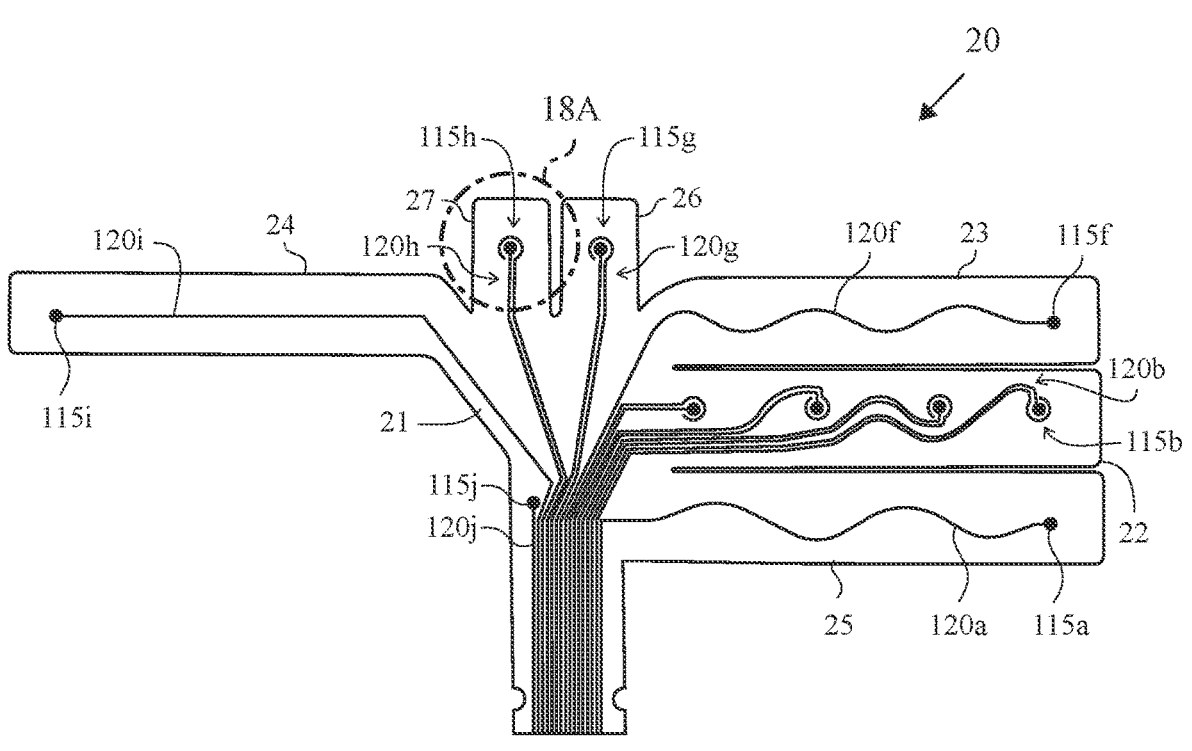
FIG. 18 is an illustration of a concentric ring electrodes embodiment.

In reference to FIGS. 14-23, in an alternative embodiment, the EXG 20 preferably comprises a body 21 and screen-printed electrodes 115. The body 21 preferably comprises a center extension member 22, a second extension member 23, a third extension member 24, a fourth extension member 25, a fifth extension member 26, and a sixth extension member 27, as shown in FIG. 18. Each of the extension members 22-27 extend outward from a center of the body 21 for proper placement of the electrodes 115 on a patient. Each extension member 22-27 preferably has a width ranging from 1 cm to 10 cm, and a length ranging from 5 cm to 20 cm. The body 21 further comprises a base layer 30 composed of a flexible material, an adhesive layer 31 composed of a flexible material, and a backing layer 32 attached to an adhesive surface 31*a* of the adhesive layer 31.

In an alternative embodiment, the EXG 20 preferably comprises a body 21, screen-printed electrodes 115, and an electrode connector cable 60 extending from the body 21. The body 21 preferably comprises a center extension member 22, a second extension member 23, a third extension member 24, a fourth extension member 25, a fifth extension member 26, a sixth extension member 27, and a seventh extension member (not shown). The body 21, shown in FIG. 23 as a cross-section, further comprises a main layer 30 having a top surface 30*a* and an adhesive surface 30*b*, and a backing layer 32 attached to an adhesive surface 31*a* of the adhesive layer 31. An electrical conducting elastic material is incorporated into the top surface 30*a*. Each of the screen-printed electrodes 115 are positioned on the adhesive surface 30*b* of the main layer 30. Each screen-printed electrode 115 is further connected to the electrode connector cable 60 through the electrical conducting elastic material of the main layer 30.

One preferred material for the flexible material is KT TAPE from Spidertech. The top layer 30 preferably has a Shore A hardness ranging from 50 to 90, which better allows for chest compressions. One preferred material for the adhesive layer is an adhesive from 3M.

Alternatively, an elastic conductive material is substituted for each of the printed wires. Such elastic conductive materials preferably comprise silver chloride and/or graphene. The body 21 is preferably composed of a kinesiology type tape.

Figure 14:
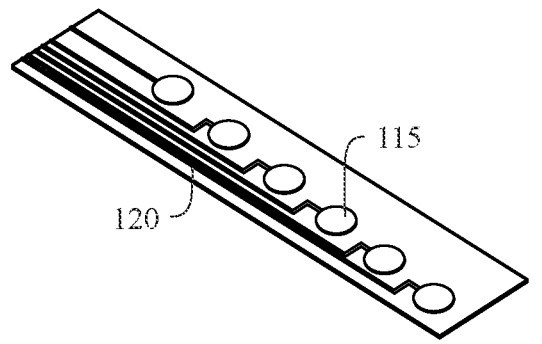
FIG. 14 is an illustration of a multi-electrode screen printed design.

A multi-electrode screen printed design with electrodes 115 and wires 120 is shown in FIG. 14.

Figure 15:
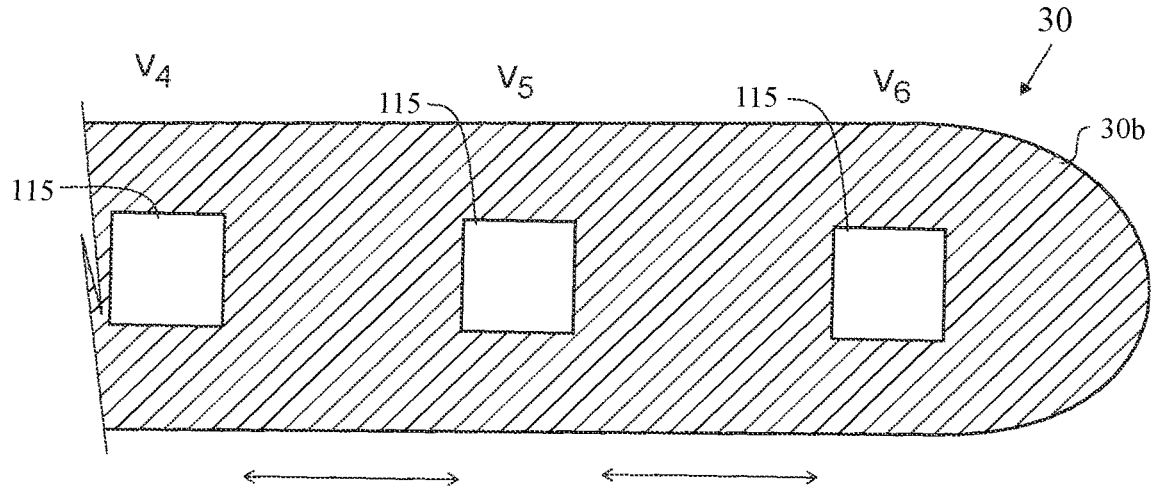
FIG. 15 is an isolated bottom plan view of a bottom surface of an extension of an emergency cardiac and ECG electrode placement device.

FIG. 15 illustrates an isolated bottom plan view of a bottom surface of an extension of an EXG device 20. The bottom adhesive surface 30*b* of the main layer 30 has electrodes 115 positioned thereon.

FIG. 16 illustrates an isolated top plan view of a top surface of an extension of the EXG device 20. The main layer 30 of the extension has a top layer 30*a* with integrated printed wires (or elastic electrical conducting material) 60*d*, 60*e* and 60*f* connected to corresponding electrodes 115*d*, 115*e* and 115*f* that are positioned on an adhesive surface below. The electrodes 115*d*, 115*e* and 115*f* are not positioned on the top surface 30*a* of the main layer 30.

Figure 19:
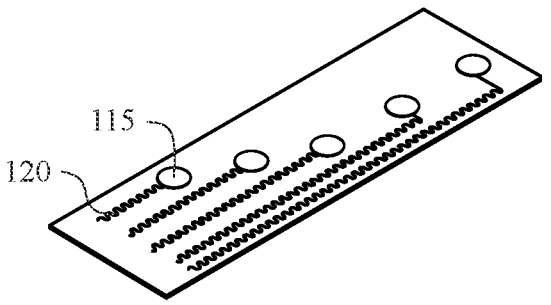
FIG. 19 is an illustration of a multi-electrode screen printed design in a serpentine embodiment.

In FIG. 19, a backbone is coated on the tape first (using Ecoflex). Wire insulation is preferably of: Dielectric Strength (ASTM D-147-97a): >350 volts/mil. A screen-printed serpentine pattern of wires 120 is created to fit V2-V6 and a stencil is made: The Ecoflex backbone is coated directly on the fabric; measure the maximum resistant and strain; take ECG measurements with these electrodes 115.

Figure 17A:
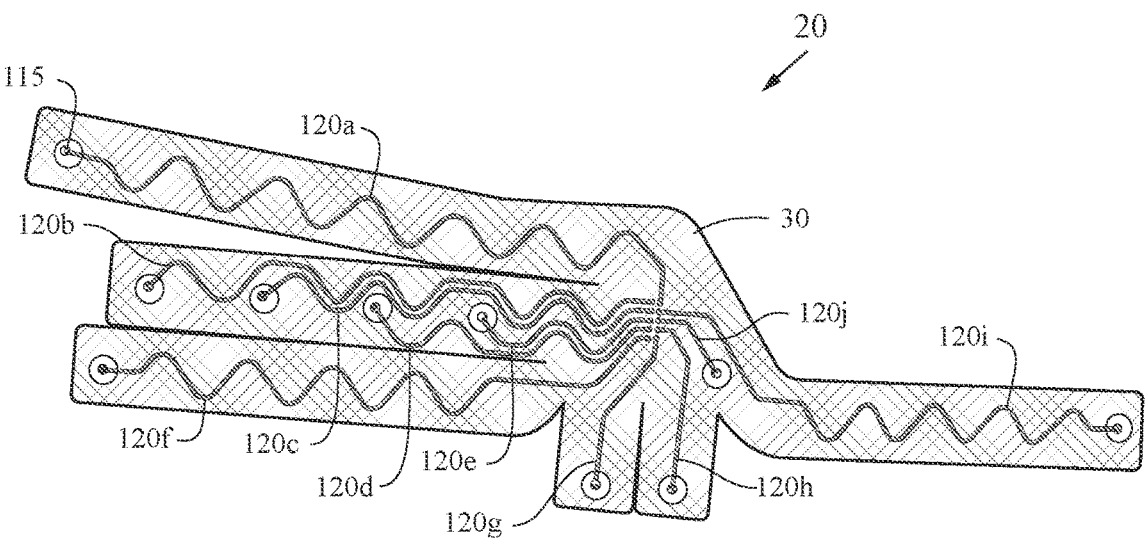
FIG. 17A is a top plan view of a multi-electrode embodiment of FIG. 17.

FIG. 17 illustrates a bottom plan view of a screen-printed electrode 115 embodiment with a serpentine design of the wires 120. An adhesive layer 31 is shown with a piece of the backing layer 32 removed. FIG. 17A illustrates a top plan view of the embodiment.

Figure 20:
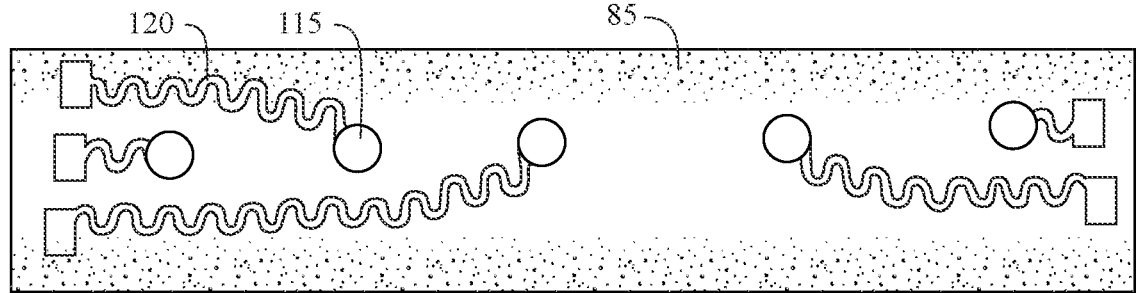
FIG. 20 is an illustration of screen-printed electrodes V2-V6.
Figure 21:
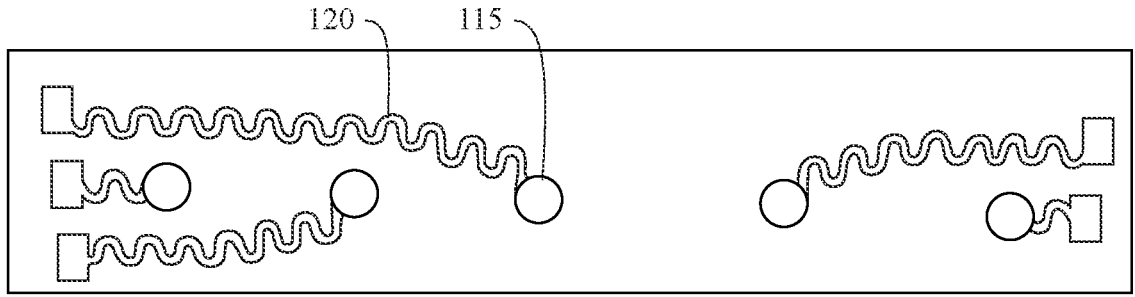
FIG. 21 is an illustration of screen-printed electrodes.
Figure 22:
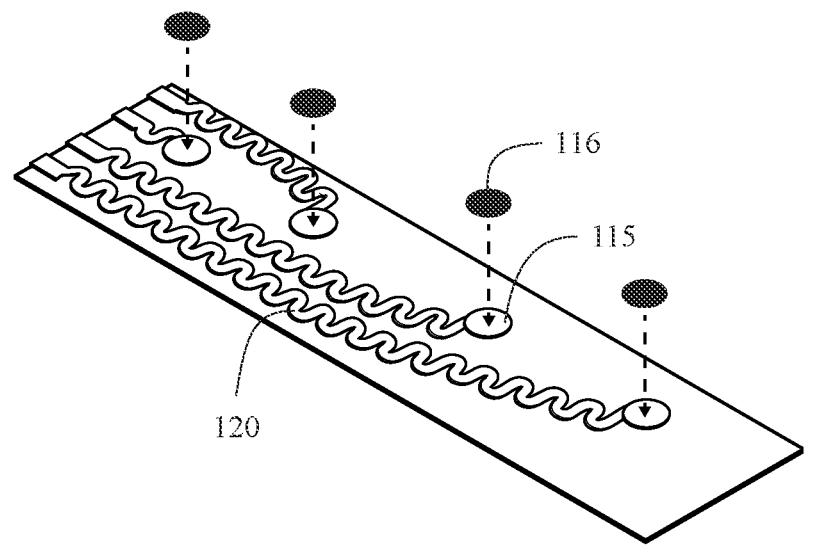
FIG. 22 is an illustration of screen-printed electrodes.
Figure 23:
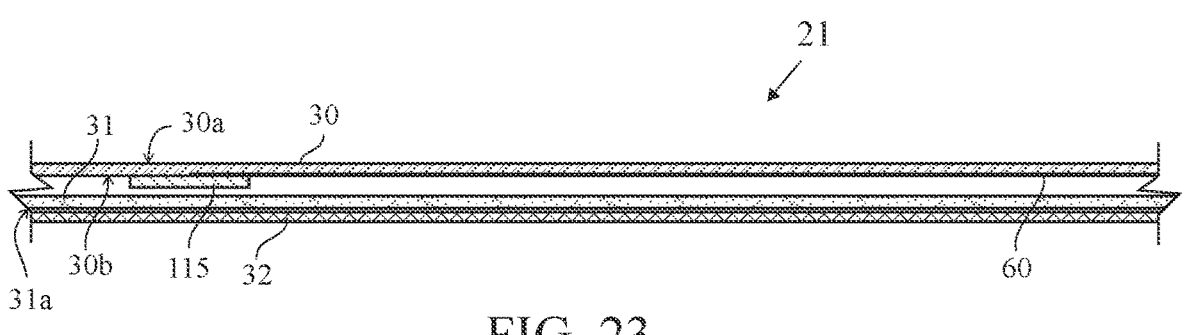
FIG. 23 is an isolated cross-sectional view of an extension and electrode of an emergency cardiac and ECG electrode placement device.
Figure 24:
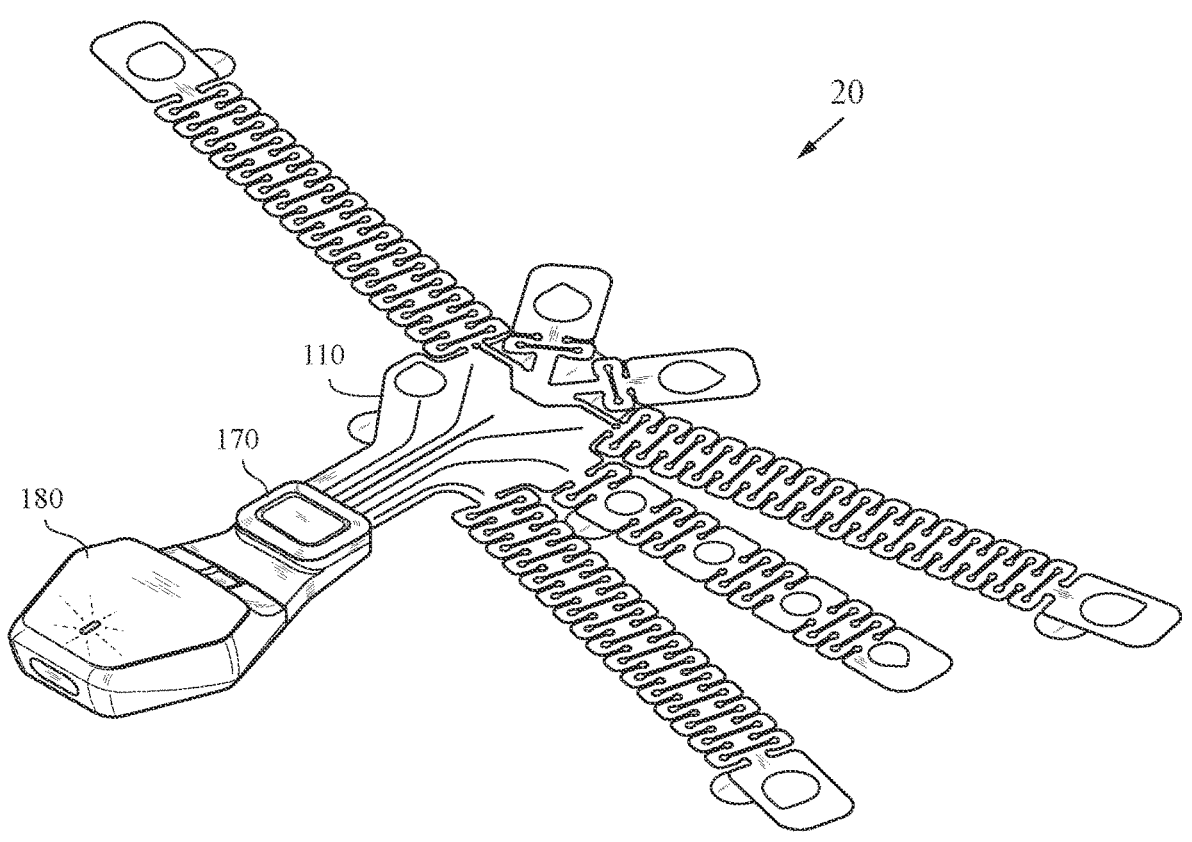
FIG. 24 illustrates a top plan view of an emergency cardiac and ECG electrode device attached to an electrode connector.

FIGS. 20-22 show a serpentine design with lowered resistance. Execution: Exoflex backbone allowed to stencil electrode on the sticky side 85 of the bandage; less ecoflex to silver ratio also reduced the resistance; evaluate the strain & make measurements with the ECG device. The electrode 115 surface is coated with hydrogel 116 to reduce interfacial resistance. Rearrange the connections and plan for connection to the lead hub (wires instead of clips). The hydrogel 116 is preferably composed of Polyvinyl Alcohol (PVA), Poly(3,4-ethylenedioxythiophene) Polystyrene Sulfonate (PEDOT:PSS) for conductivity.

Figure 18A:
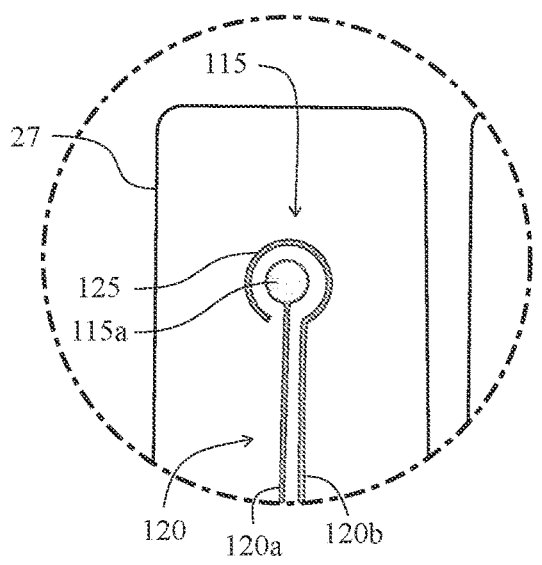
FIG. 18A is an isolated view of a multipolar electrode of FIG. 18.

FIG. 18 and FIG. 18A illustrate an ECG device 20 with screen-printed bipolar electrodes 115 embedded into a body 21 at precordial locations. The device 20 preferably comprises a body 21 and screen-printed bipolar electrodes 115. The body 21 preferably comprises center extension members 26-27 for V1 and V2, a third extension member 25, a fourth extension member 24, a fifth extension member 23, and a sixth extension member 22. Each of the extension members 22-27 extend outward from a center of the body for proper placement of the screen-printed electrodes 115 on a patient. Screen-printed wires 120a-120j connect the screen-printed electrodes 115a-115j to the central connector module 170 (module shown in FIG. 24).

Figure 18B:
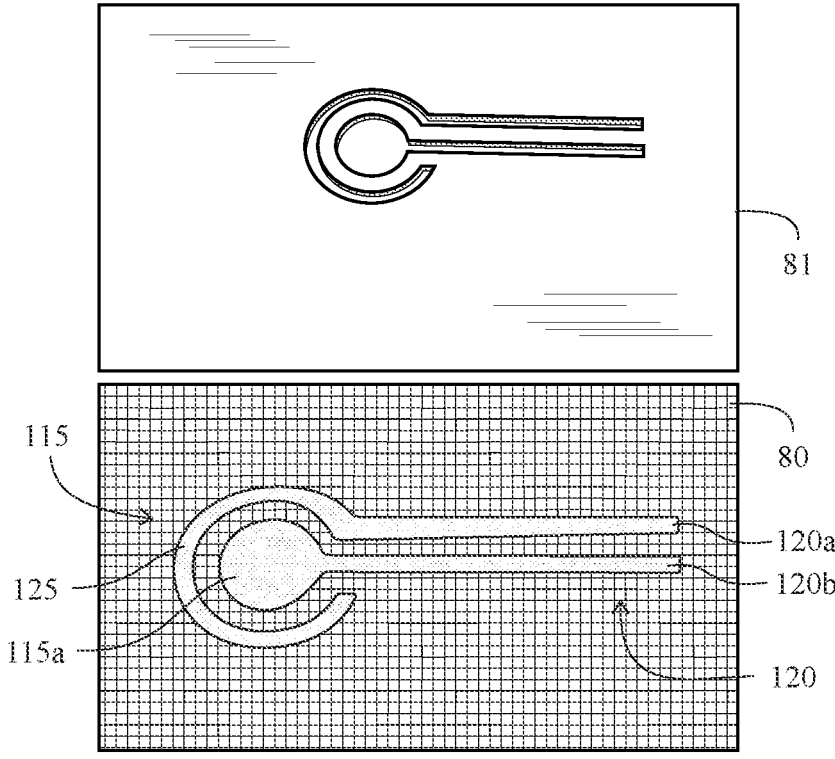
FIG. 18B is a screen-printed concentric electrode embodiment with an uniaxial strain silver and ecoflex with a stencil coated on the back of the tape.

FIGS. 18A-B shows a screen printed concentric electrode embodiment with an uniaxial strain silver and ecoflex with a stencil 81 coated on the back of the tape 80. The screen-printed concentric electrodes 115 have a first section 115a and 120b, encompassed by a second section 120a and 125. They are preferably stretchable (30% strain), and adhesive without using conductive gel. The electrodes are fixed on one bandage (to avoid user confusion on lead placement/connection). The electrical shielding for the electrode band preferably shields against high voltage of defibrillator (2500-5000 V, typical current ~20A, biphasic 200J over 10 ms). The wiring design minimizes signal distortion under mechanical strain.

Acquisition of electrode signal from skin surface potentials is enhanced with the use of concentric ring electrodes in multipolar format that is also redundant with AHA recommendations for electrode positioning. By utilizing a redundant design of unipolar electrodes 115a in AHA positions and then adding concentric ring electrodes 125, as shown in FIGS. 18A-B, to those same positions, a LaPlacian electrocardiography is provided; thus allowing for traditional ECG interpretation and enhancing this data with LaPlacian measures that improve the diagnostic performance. These multipolar (bipolar, tripolar, etc.) designs enhance the signal quality from the body surface potentials. The EXG system can utilize concentric ring electrodes to capture more detailed electrical activity of the heart and thereby obtain data that can be used for real-time analysis and further machine learning/artificial intelligence allowing for predictive analytics to be applied for earlier recognition of disease prior to meeting the ECG criteria of those events.

The ECG device 20 reduces the time to perform ECG testing significantly. A user can anticipate ECG acquisition in less than one minute, and potentially within seconds. Current ECG data can take several minutes or longer depending on the care setting. It is not unusual for an ECG ordered in a hospital setting to take more than 10-30 minutes.

The ECG device 20 solves the problem of lead detachment, lead reversal, inability to apply leads due to extremes in physiology, and lack of reproducibility to measure subtle changes. The ease of use with EXG allows for acquisition of ECGs that would not have been obtained and therefore limits the opportunity loss of delays in diagnosis and treatment. The use of an elastic pourable or printable or otherwise applied film of elastic conductive material will replace bulky standard cables and wires allowing for a more compact form, smaller footprint, and contribute to less material and weight of the device.

The ECG device 20 makes ECG data more reliable and reproducible. There is no variation in lead placement while performing serial ECGs, which is often done in the hospital and pre-hospital setting. The incorporated elastic electro-conductive materials allow for this small form factor to accommodate varying body types (man, women, adult, child, obese, anorexic) while maintaining strict anatomic ratios and correct placement and ensure proper lead placement.

In use, one applies the ECG device 20 to an anterior chest wall overlying the sternum symmetrically at a level above the nipple line of the patient and below the sternal notch, removing the backing layer to expose the adhesive surface of the adhesive layer. The precordial limb is then stretched to the lateral chest wall at the mid axillary line below the nipple line. Similarly, each limb will have the backing layer removed in succession to expose the adhesive surface of the adhesive layer. The right upper extremity limb (RA) is stretched towards the right shoulder. The left upper extremity limb (LA) is stretched towards the left shoulder. The left lower extremity limb (LL) is stretched to the left lower abdominal quadrant. The cable is either attached to directly to the ECG device cable. Or in versions utilizing a BLUETOOTH transceiver, then the ECG device 20 is activated to sync with the BLUETOOTH transceiver that is already connected to the ECG device.

In one embodiment, a data cable brings individual electrodes into one cable that encompasses a minimum of ten wires/leads of the typical ECG analysis which is then compatible with various ECG devices and wireless transfer system. Other conductive interfaces may be utilized with the invention including ones composed of graphene/carbon, nickel, and copper.

In an alternative embodiment, the ECG device 20 comprises a wireless emitter and a wireless receiver. The wireless emitter is connected to electrode cable connector, and the wireless receiver is connected to an ECG machine. The wireless emitter and the wireless receiver preferably operation on a BLUETOOTH communication protocol. However, those skilled in the pertinent art will recognize that other wireless communication protocols may be utilized with the alternative embodiment of the ECG device 20 without departing from the scope and spirit of the present invention.

Another embodiment has a posterior extension member which preferably has multiple electrodes that connect via a cable to an intermediary adapter module which connects to the electrode cable connector. The posterior leads preferably are connected through the adapter module onto the end of the original ECG device 20 and basically take over leads V5-6 for the standard ECG.

In another embodiment, the ECG device 20 also preferably comprises a plurality of external electrodes.

In one embodiment, the stretching capability of the extension members of the ECG device 20 preferably extends from a length L1 ranging from 7.0 to 14.0 inches to a length L2 ranging from 10.0 to 16.5 inches. In a most preferred embodiment, L1 ranges from 10 to 11 inches, and L2 ranges from 12 to 13 inches. A width of each extension member 22, 23, 24, 25, 26 preferably ranges from 1 cm to 10 cm, and most preferably 2.5 cm to 5 cm. A thickness of each extension member 22, 23, 24, 25, 26 preferably ranges from 0.1 inch to 0.5 inch.

A preferred source for the printed wires is PE874 conductor ink from Intexar Dupont. Those skilled in the pertinent art will recognize that other printed electrically conductive materials may be used without departing from the scope and spirit of the present invention.

The electrodes include a multitude of designed electrodes to improve signal to noise ratio through use of designs which limit wire movement and improved signal processing from skin electrodes which are designed with bipolar and tripolar concentric ring electrodes. These electrodes are flexible and elastic with improved spatial resolution. They are printable by methods of screen printing and methods of 3D printing directly to fabric. The design of the interface between the electrode and the lead is optioned to allow for exchange/replacement of electrodes which offers re-useablity. The flexible electronic composition allows for conformity to various body habitus while preserving the integrity of signal quality at rest and in motion.

The ECG device captures data from subjects that is then transmitted to local, networked and cloud based machines.

An electrode allows for the acquisition of superficial electrical activity.

A wireless electrode interface carries the electrical activity to a transmitter or device directly.

A powered transmitter is a long-life Battery Powered Wireless analog-to-analog or analog-to-digital transmission with or without amplification, or alternatively, a direct powered connection between transmitter and receiver with or without amplification through a direct machine connection.

A powered receiver is a long-life Battery Powered Wireless analog-to-analog or digital-analog receiver with or without amplification.

A direct wired connector is a wire to ECG machine interface, multi-pin connector with or without amplification.

Figure 31:
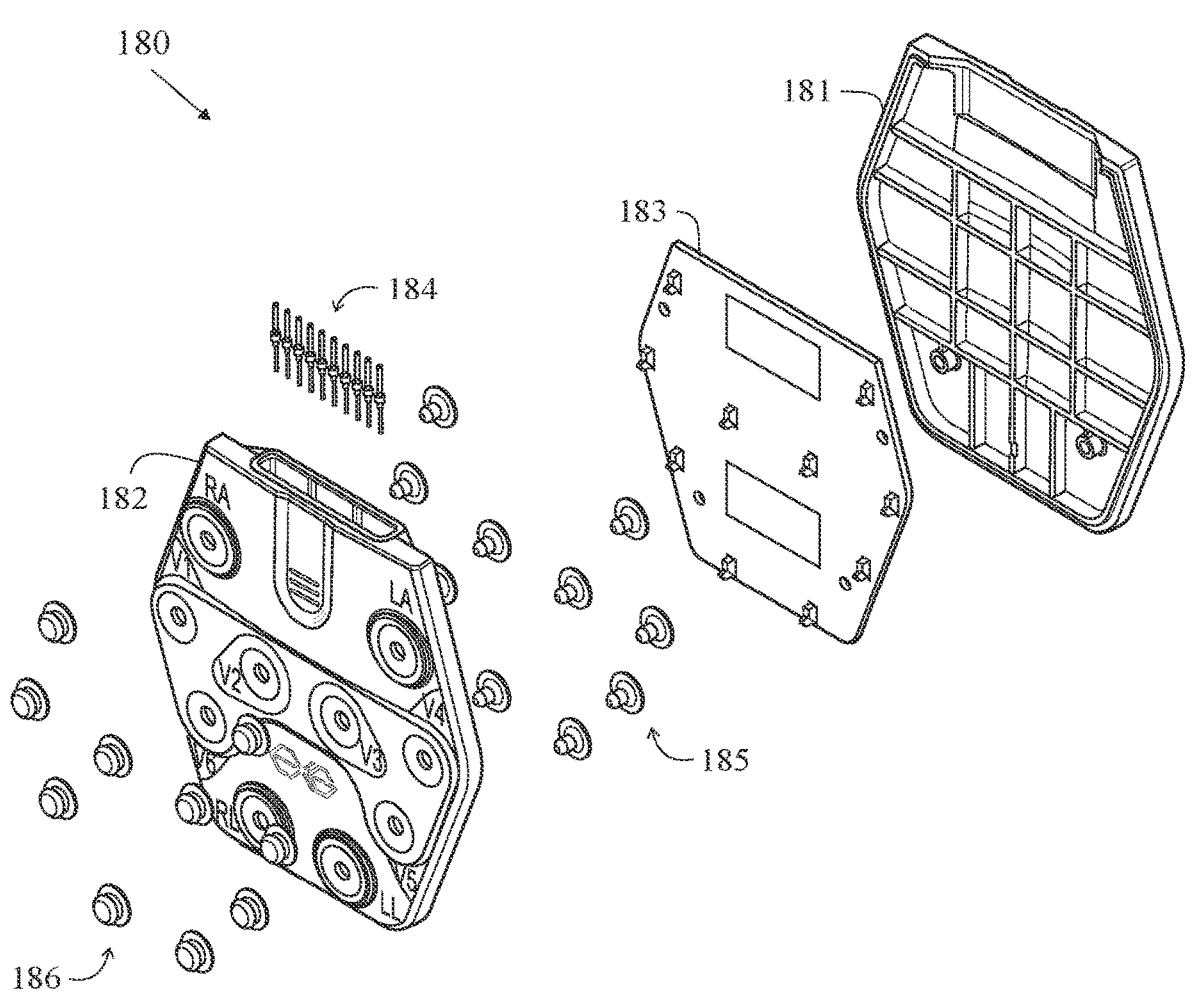
FIG. 31 is an exploded view of a 12 lead snap adapter.
Figure 32:
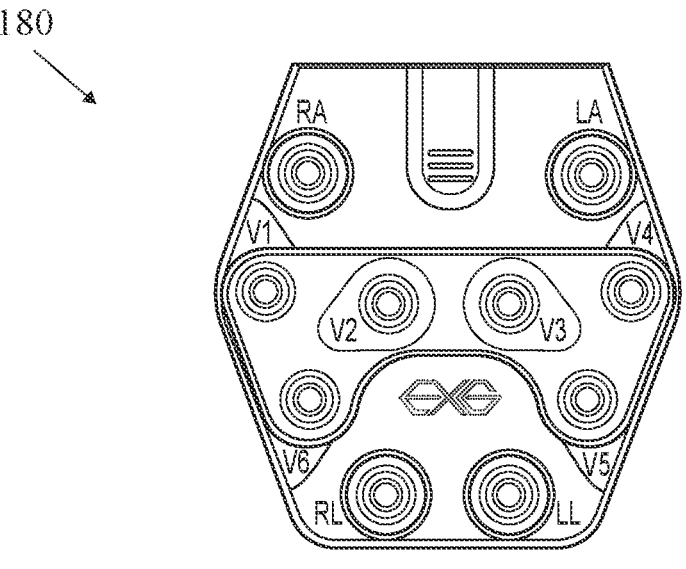
FIG. 32 is a top view of a 12 lead snap adapter.
Figure 33:
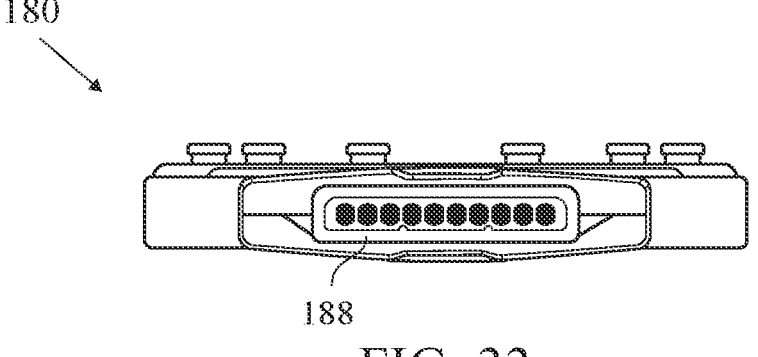
FIG. 33 is a front view of a 12 lead snap adapter.
Figure 34:
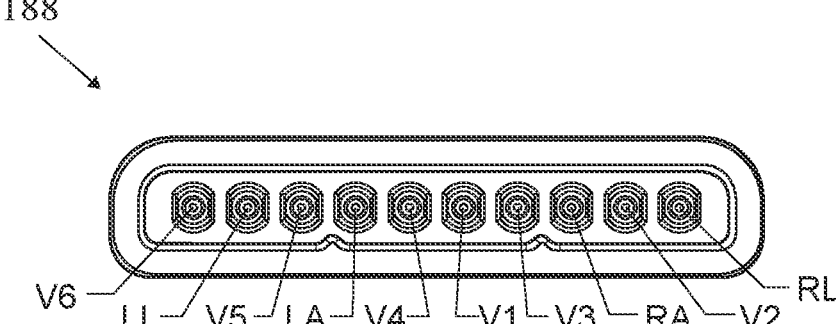
FIG. 34 is an isolated view of a 12 lead snap adapter of FIG. 33.

A universal adapter 180, as shown in FIG. 31, is comprised of a bottom casing 181, an upper casing 182, a PCBA 183, press fit pins 184, fastener eyelets 185, and fastener studs 186. FIGS. 32-34 show a wiring diagram of a universal adapter 180, which is preferably a universal 12 lead snap adapter. A connection port 188 is shown in FIGS. 33 and 34. The connection port 188 preferably has a length ranging from 30 millimeters (mm) to 40 mm, and a height ranging from 3 to 6 mm. The universal adapter 180 allows for connection of the ECG device 20 to a standard ECG apparatus by connecting to the fastener studs 186. The universal adapter 180 preferably has a length ranging from 80 to 100 mm, a width preferably ranging from 75 to 85 mm, and a height preferably ranging from 10-15 mm.

Figure 28:
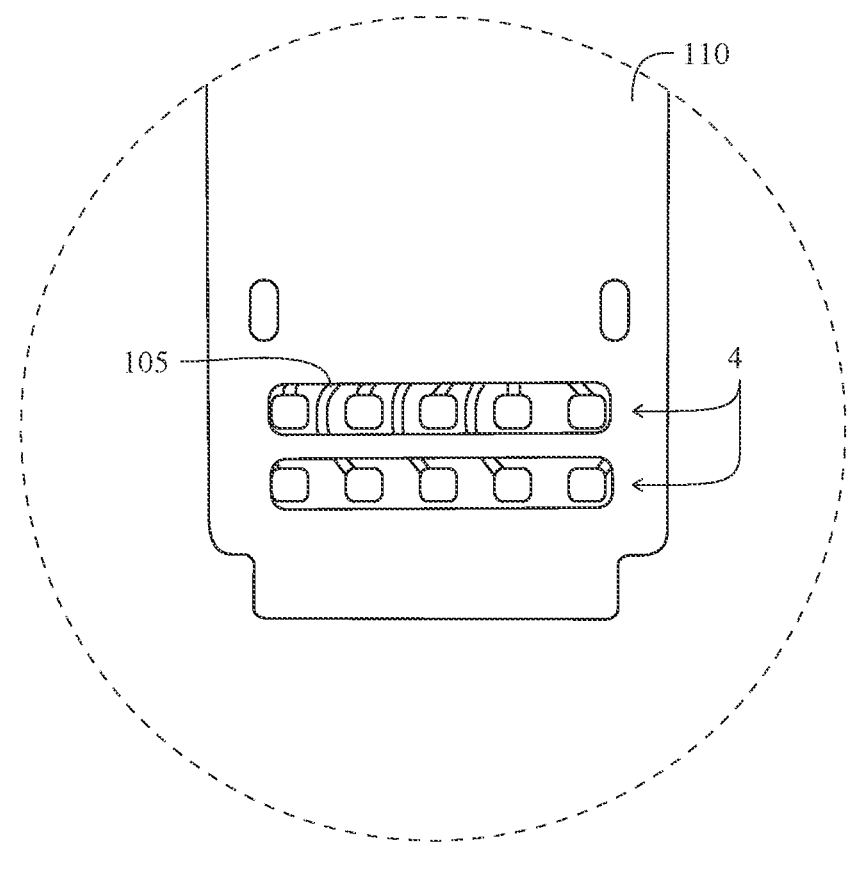
FIG. 28 is an enlarged isolated bottom plan view of an end of the ECG device.
Figure 29:
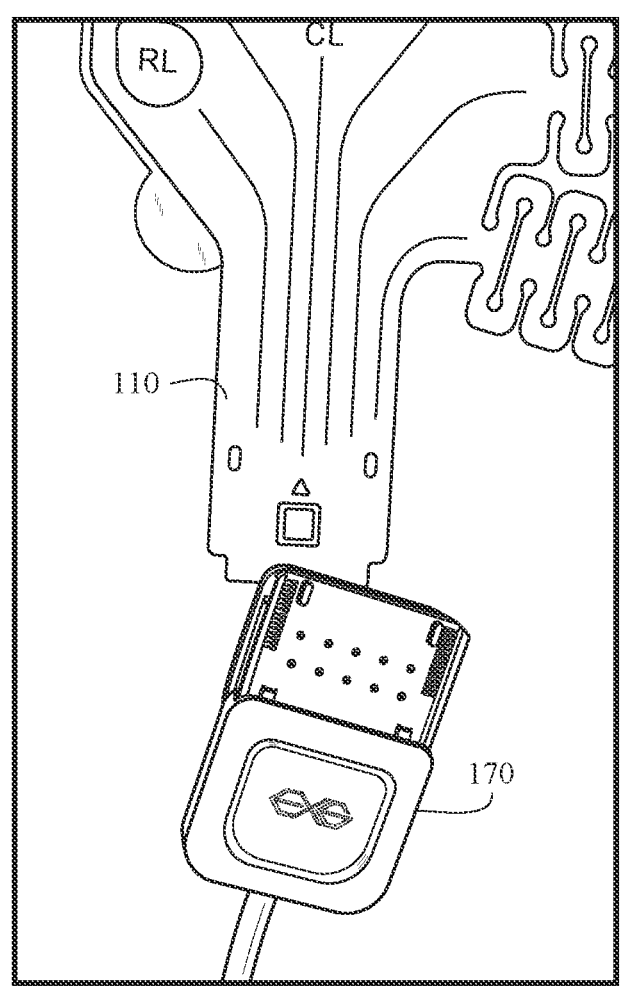
FIG. 29 is an isolated view of the end of the device and the electrode connector prior to connection.
Figure 30:
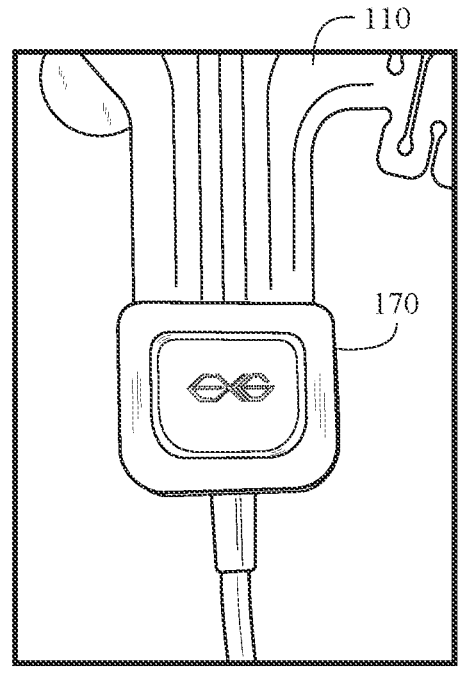
FIG. 30 is an isolated view of the end of the device and the electrode connector.
Figure 35:
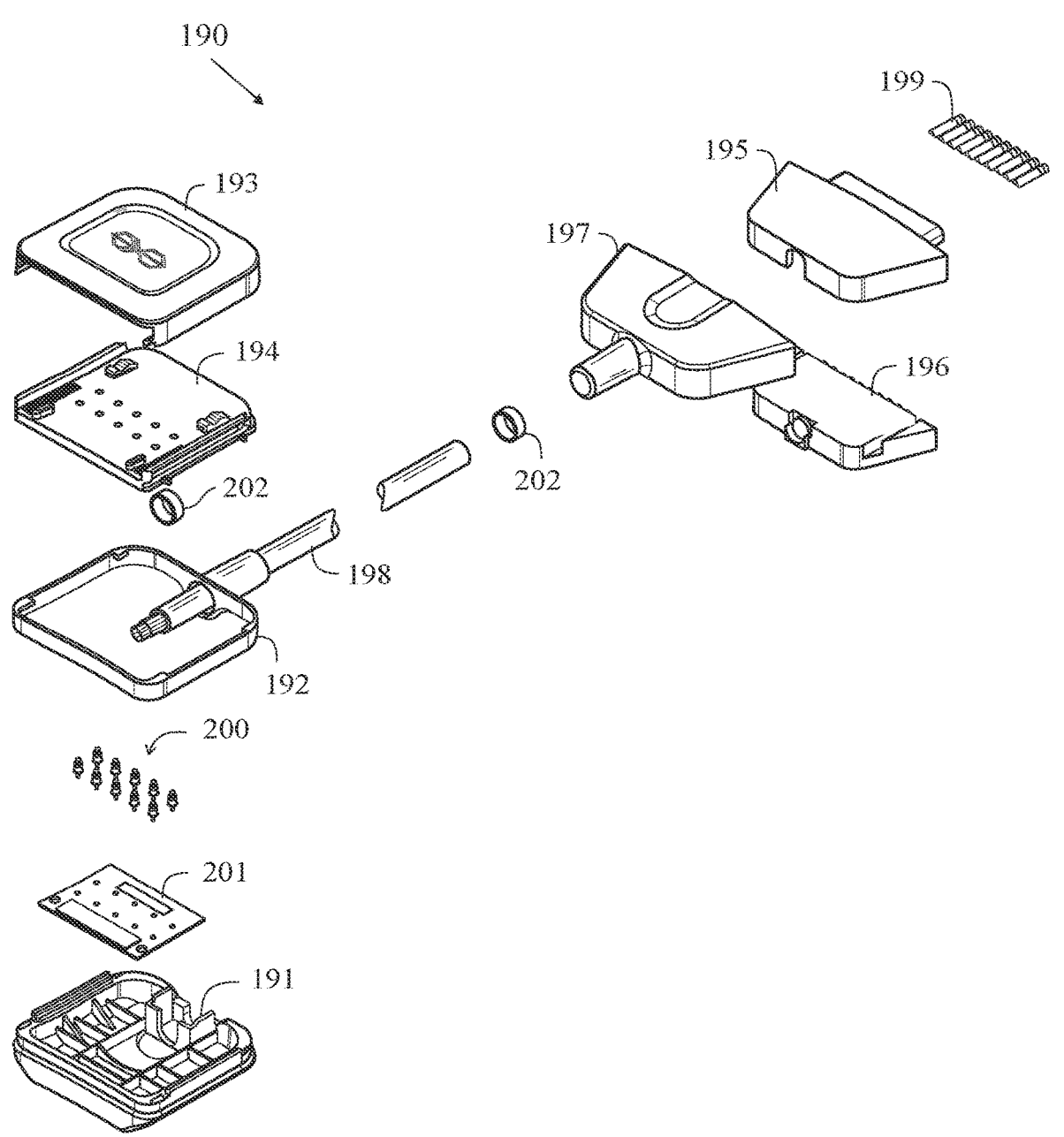
FIG. 35 is an exploded view of a stress test adapter.
Figure 36:
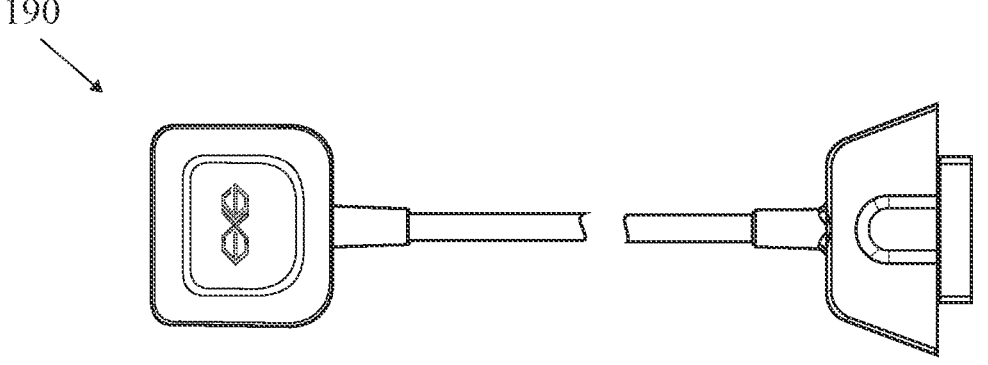
FIG. 36 is a top view of a stress test adapter.

FIGS. 35-39 illustrate a stress test adaptor 190. As shown in FIGS. 28-30, the stress test adaptor connects to an end of the lower extension of the body 110 of the ECG device 20. The stress test adapter 190, as shown in FIG. 35, is comprised of a stress cable adapter body 191, an adapter overmold resin 192, a top cap 193, a chassis blanking plate 194, a stress cable connector 195, a connector premold resin 196, a connector overmold resin 197, a wire jacket 198, a cup socket 199, pogo pins 200, a bare board 201, and copper crimp rings 202. FIG. 36 shows an assembled stress test adapter 190. As shown in FIG. 28, carbon contacts 4 are connected to corresponding screen printed wires 105. Each of the carbon contacts 4 are aligned with a corresponding pin of the plurality of pogo pins 200. As shown in FIG. 29, holes in the end of the lower extension of the body 110 of the ECG device 20 align with projections on the chassis blanking plate 194 to fit the ECG device 20 to the electrode connector 170 of the stress test adapter 190. As shown in FIG. 30, the top cap 193 is slid over the end of the lower extension of the body 110 of the ECG device 20 to securely connect the ECG device 20 to the electrode connector 170. The electrode connector 170 preferably has a length ranging from 35 to 45 mm, and preferably a width ranging from 40 to 50 mm.

Figure 37:
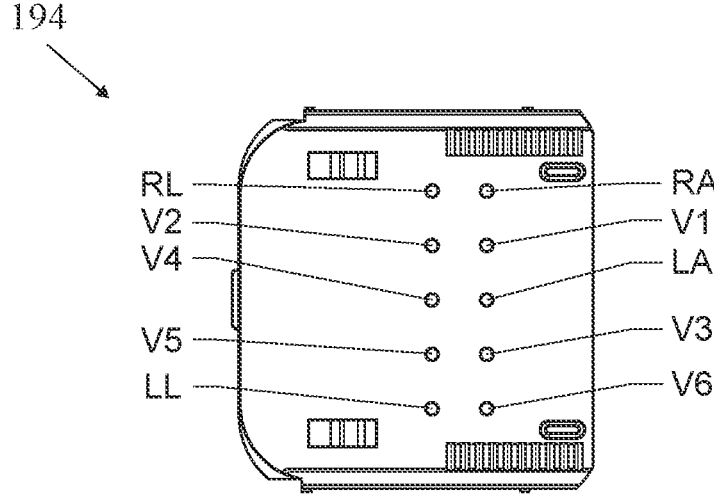
FIG. 37 is an isolated view of a component of a stress test adapter.
Figure 38:
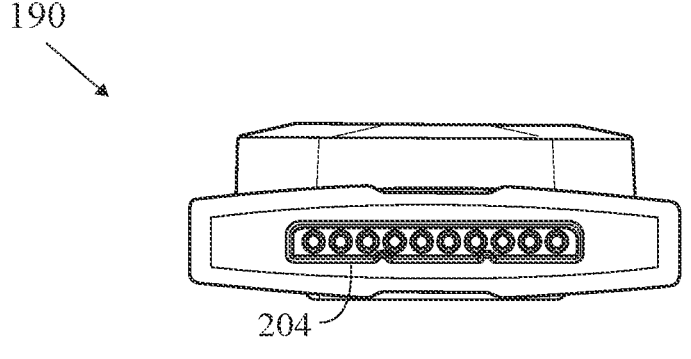
FIG. 38 is a front view of a stress test adapter.
Figure 39:
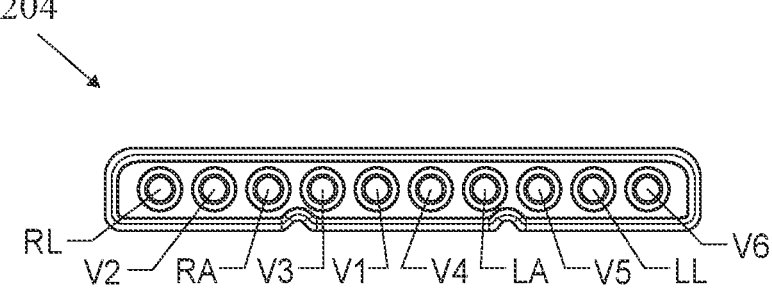
FIG. 39 is an isolated view of a stress test adapter of FIG. 38.

FIGS. 37-39 illustrate a wiring of the stress test adapter 190. A connection extension 204 preferably mates with the connection port 188 of the universal adaptor 180.

Figure 40:
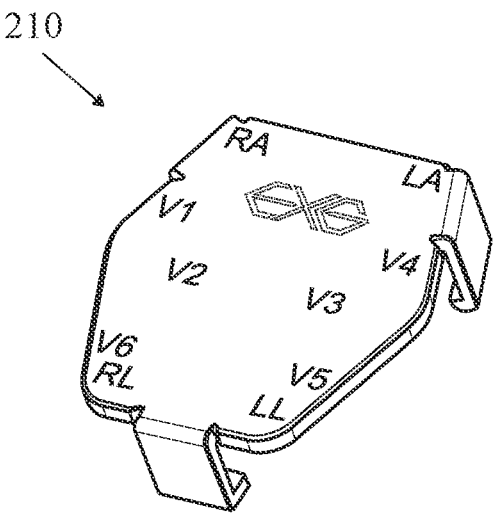
FIG. 40 is a top perspective view of a cover for the universal adaptor.

FIG. 40 is a top perspective view of a cover 210 for the universal adaptor 180. The cover 210 protects the attached wires to the studs 186. The cover 210 has a snap-on design. The cover is preferably composed of a plastic material.

A conductive elastic rubber material is disclosed in U.S. Pat. No. 8,491,884, which pertinent parts are hereby incorporated by reference.

A stretchable graphene film material is disclosed in Chen et al., U.S. Patent Publication Number 20150273737, which pertinent parts are hereby incorporated by reference.

A flexible conductive material comprising silver is disclosed in Taguchi et al., U.S. Patent Publication Number 20130056249, which pertinent parts are hereby incorporated by reference.

Dunphy et al., U.S. Pat. No. 9,986,929 for an Emergency Cardiac And Electrocardiogram Electrode Placement System is hereby incorporated by reference in its entirety.

Dunphy et al., U.S. patent Ser. No. 10/893,818 for an Emergency Cardiac And Electrocardiogram Electrode Placement System is hereby incorporated by reference in its entirety.

Dunphy et al., U.S. Pat. No. D872279 for an Emergency Cardiac And Electrocardiogram Electrode Placement System is hereby incorporated by reference in its entirety.

Ronan et al., U.S. Pat. No. D877912, for a Cable Controller For An Electrocardiogram Electrode Placement System is hereby incorporated by reference in its entirety.

McClung et al., U.S. patent application Ser. No. 16/428,927, filed on May 31, 2019, for an Emergency Cardiac And Electrocardiogram Electrode Placement System With Artificial Intelligence is hereby incorporated by reference in its entirety.

McClung et al., U.S. patent application Ser. No. 16/428,984, filed on Jun. 1, 2019, for an Emergency Cardiac And Electrocardiogram Electrode Placement System With Wireless Electrodes is hereby incorporated by reference in its entirety.

McClung et al., U.S. patent application Ser. No. 16/812,330, filed on Mar. 8, 2020, for a Wearable Diagnostic Electrocardiogram Garment is hereby incorporated by reference in its entirety.

McClung et al., U.S. Patent Publication Number 2022017592 (U.S. patent application Ser. No. 17/665,003, filed on Mar. 8, 2020) for a Screen Printed Electrodes For An Electrocardiogram Article is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. An emergency cardiac and electrocardiogram (ECG) electrode placement device, the device comprising:

a body comprising a plurality of extension members, wherein the body comprises a base layer composed of an unwoven fabric material, an adhesive layer composed of a flexible material, and a backing layer attached to an adhesive surface of the adhesive layer, a first extension member of the plurality of extension members comprises a first extension section and a first electrode section having a first printed electrode, the first extension section comprising a plurality of concertina members and a plurality of connector members wherein an end connector member of the plurality of connector members connects an end concertina member to the first electrode section, wherein the first extension member has an un-extended state length ranging from 20-30 centimeters (cm) and a width ranging from 1-4 cm, a second extension member of the plurality of extension members comprises a second expansion section adjacent a second printed electrode section having a second electrode, a third expansion section adjacent a third printed electrode section having a third electrode, a fourth expansion section adjacent a fourth printed electrode section having a fourth electrode, and a fifth expansion section adjacent a fifth electrode section having a fifth printed electrode, wherein the second extension member has an un-extended state length ranging from 15-25 centimeters (cm) and a width ranging from 1-4 cm, a third extension member of the plurality of extension members comprises a sixth extension section and a sixth electrode section having a sixth printed electrode, the sixth extension section comprising a plurality of concertina members and a plurality of connector members wherein an end connector member of the plurality of connector members connects an end concertina member to the sixth electrode section, wherein the third extension member has an un-extended state length ranging from 20-30 centimeters (cm) and a width ranging from 1-4 cm, a fourth extension member of the plurality of extension members comprises a seventh extension section and a seventh electrode section having a seventh printed electrode, wherein the seventh extension section comprises a single concertina member and single connection member, wherein the fourth extension member has an un-extended state length ranging from 3-10 centimeters (cm) and a width ranging from 1-4 cm,

a fifth extension member of the plurality of extension members comprises an eighth extension section and an eighth electrode section having an eighth printed electrode, wherein the eighth extension section comprises a single concertina member and single connection member, wherein the eighth extension member has an un-extended state length ranging from 3-10 centimeters (cm) and a width ranging from 1-4 cm, a sixth extension member of the plurality of extension members comprises a ninth extension section and a ninth electrode section having a ninth printed electrode, the ninth extension section comprising a plurality of concertina members and a plurality of connector members wherein an end connector member of the plurality of connector members connects an end concertina member to the ninth electrode section, wherein the sixth extension member has an un-extended state length ranging from 20-30 centimeters (cm) and a width ranging from 1-4 cm; and a central body having a tenth printed electrode wherein each of the plurality of extension members extend outward from the central body for proper placement of the ten printed electrodes on a patient.

2. The emergency cardiac and ECG electrode placement device according to claim 1 further comprising a plurality of printed wires, each of the plurality of ten printed electrodes connected to a printed wire of the plurality of printed wires.

3. The emergency cardiac and ECG electrode placement device according to claim 2 wherein each of the plurality of printed wires and each of the ten printed electrodes is composed of a printable conductive silver.

4. The emergency cardiac and ECG electrode placement device according to claim 1 further comprising a plurality of contacts positioned on an end portion of the center section of the central body, each of the plurality of contacts composed of an abrasive resistant ink.

5. The emergency cardiac and ECG electrode placement device according to claim 1 wherein each of the plurality of extension members is configured for at least double length extension from an un-extended state.

* * * * *